United States Patent
Prudhomme et al.

(10) Patent No.: US 7,151,108 B2
(45) Date of Patent: Dec. 19, 2006

(54) [3,4-A:3,4-C]CARBAZOLE COMPOUNDS

(75) Inventors: Michelle Prudhomme, Clermont-Ferrand (FR); Bernadette Hugon, Clermont-Ferrand (FR); Fabrice Anizon, Ennezat (FR); John Hickman, Paris (FR); Alain Pierre, Les Alluets le Roi (FR); Roy Golsteyn, Maurecourt (FR); Pierre Renard, Le Chesnay (FR); Bruno Pfeiffer, Saint Leu la Foret (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 333 days.

(21) Appl. No.: 10/672,418

(22) Filed: Sep. 26, 2003

(65) Prior Publication Data

US 2004/0077672 A1 Apr. 22, 2004

(30) Foreign Application Priority Data

Oct. 16, 2002 (FR) ................... 02 12847

(51) Int. Cl.
- *A61K 31/437* (2006.01)
- *A61K 31/403* (2006.01)
- *C07D 471/22* (2006.01)
- *C07D 487/14* (2006.01)
- *C07D 491/14* (2006.01)

(52) U.S. Cl. ................. 514/280; 514/410; 546/48; 548/418

(58) Field of Classification Search ............... 548/418; 514/410, 280; 546/48
See application file for complete search history.

(56) References Cited

OTHER PUBLICATIONS

Bergman et al., Acid-induced dimerization of 3-(1H-indol-3-yl)maleimides. Formation of cyclopentindole derivatives., J. Chem. Soc., Perkin Trans. 1, 2000, 2615-2621.*

Cancer and Metastasis Reviews (1998), 17(1), 91-106.*
Science (1999), vol. 286, 531-537.*

* cited by examiner

*Primary Examiner*—Joseph K. McKane
*Assistant Examiner*—Rebecca Anderson
(74) *Attorney, Agent, or Firm*—Hueschen and Sage

(57) ABSTRACT

A compound selected from those of formula (I):

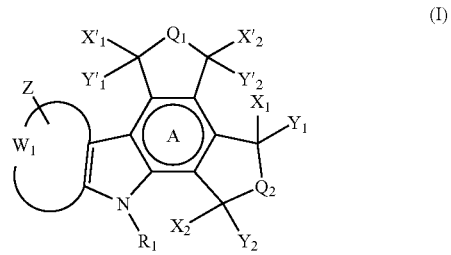

wherein:

$W_1$ represents, together with carbon to which it is bonded, phenyl, pyridyl,

Z represents a group of formula U—V as defined in the description, $Q_1$ represents oxygen, $NR_2$ as defined in the description, $Q_2$ represents oxygen, $NR'_2$ as defined in the description, $X_1$, $X_2$, $X'_1$ and $X'_2$ each represents hydrogen, hydroxy, alkoxy, mercapto or alkylthio, $Y_1$, $Y_2$, $Y'_1$ and $Y'_2$ each represents hydrogen, or $X_1$ and $Y_1$, $X_2$ and $Y_2$, $X'_1$ and $Y'_1$, $X'_2$ and $Y'_2$ with carbon carrying them, together form carbonyl or thiocarbonyl, $R_1$ is as defined in the description, its isomers, and addition salts thereof with a pharmaceutically acceptable acid or base, and medicinal products containing the same which are useful in the treatment of cancer.

20 Claims, No Drawings

[3,4-A:3,4-C]CARBAZOLE COMPOUNDS

FIELD OF THE INVENTION

The needs of anti-cancer therapy call for the constant development of new anti-proliferative agents, with the aim of obtaining medicaments that are both more active and better tolerated. The compounds of the present invention exhibit in particular anti-tumour properties, which accordingly render them useful in the treatment of cancers. Among the types of cancer that can be treated with the compounds of the present invention there may be mentioned, without implying any limitation, adenocarcinomas and carcinomas, sarcomas, gliomas and leukaemias. By virtue of their properties, the compounds of the invention can advantageously be associated with all cytotoxic treatments currently in use, as well as with radiotherapies, whose toxicity is not increased thereby, and with the various hormone therapies directed against cancers (blood and prostate).

DESCRIPTION OF THE PRIOR ART

The Patent Applications WO 95/07910 and WO 96/04906 describe indole compounds and claim them, on the one hand, for their antiviral activity and, on the other hand, for the treatment and prevention of restenosis. The Patent Applications WO 00/47583, WO 97/21677 and WO 96/11933 disclose cyclopenta[g]pyrrolo[3,4-e]indole compounds which are fused on the indole moiety and the cyclopentene moiety of the compounds to an aromatic or non-aromatic ring system and which optionally contain hetero atoms. Those compounds exhibit pharmacological properties that render them useful especially in the treatment of cancer. Patent Application WO 01/85686 describes pyrrolo[3,4-c]carbazole compounds for use in the treatment of neurodegenerative diseases, inflammation, ischaemia and cancer. Patent Application WO 02/24699 describes tetrahydrocarbazole compounds for use on the one hand in antimicrobial treatment and on the other hand as a deodorant and disinfectant of the skin.

DETAILED DESCRIPTION OF THE INVENTION

The present invention relates more especially to compounds of formula (I):

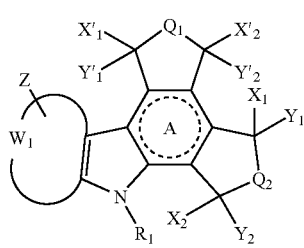

(I)

wherein:
A represents a saturated or partially or fully unsaturated ring, wherein the unsaturation optionally confers an aromatic nature on the ring,
$W_1$, together with the carbon atoms to which it is bonded, represents a phenyl group or a pyridyl group,
Z represents one or more identical or different groups of formula U—V wherein:

U represents a single bond, a linear or branched $(C_1-C_6)$alkylene chain or a linear or branched $(C_2-C_6)$alkenyl chain optionally substituted by one or more identical or different groups selected from halogen and hydroxy, and/or optionally containing one or more unsaturated bonds, V represents a group selected from a hydrogen atom, a halogen atom and the groups cyano, nitro, azido, linear or branched $(C_1-C_6)$alkyl, aryl, aryl-$(C_1-C_6)$alkyl in which the alkyl moiety may be linear or branched, hydroxy, linear or branched $(C_1-C_6)$alkoxy, aryloxy, aryl-$(C_1-C_6)$alkoxy in which the alkoxy moiety may be linear or branched, formyl, carboxy, aminocarbonyl, $NR_3R_4$, —C(O)-$T_1$, —C(O)—$NR_3$-$T_1$, —$NR_3$—C(O)-$T_1$, —O—C(O)-$T_1$, —C(O)—O-$T_1$, —$NR_3$-$T_2$-$NR_3R_4$, —$NR_3$-$T_2$-$OR_3$, —$NR_3$-$T_2$-$CO_2R_3$, —O-$T'_2$-$NR_3R_4$, —O-$T'_2$-$OR_3$, —O-$T'_2$-$CO_2R_3$, and —S(O)$_t$—$R_3$, wherein
$R_3$ and $R_4$, which may be indentical or different, each represents a group selected from a hydrogen atom and the groups linear or branched $(C_1-C_6)$alkyl, aryl, and aryl-$(C_1-C_6)$alkyl in which the alkyl moiety may be linear or branched, or $R_3$+$R_4$, with the nitrogen atom carrying them, together form a saturated monocyclic or bicyclic heterocycle that has from 5 to 10 ring atoms, optionally contains in the ring system a second hetero atom selected from oxygen and nitrogen, and is optionally substituted by a group selected from linear or branched $(C_1-C_6)$alkyl, aryl, aryl-$(C_1-C_6)$alkyl in which the alkyl moiety may be linear or branched, hydroxy, linear or branched $(C_1-C_6)$alkoxy, amino, linear or branched mono-$(C_1-C_6)$alkylamino, and di$(C_1-C_6)$alkylamino in which the alkyl moieties may be linear or branched, $T_1$ represents a group selected from linear or branched $(C_1-C_6)$alkyl that is optionally substituted by a group selected from —$OR_3$, —$NR_3R_4$, —$CO_2R_3$, —$C(O)R_3$ and —$C(O)NR_3R_4$ wherein $R_3$ and $R_4$ are as defined hereinbefore; aryl, and aryl-$(C_1-C_6)$alkyl in which the alkyl moiety may be linear or branched; or $T_1$ represents a linear or branched $(C_2-C_6)$alkenyl chain optionally substituted by a group selected from —$OR_3$, —$NR_3R_4$, —$CO_2R_3$, —$C(O)R_3$ and —$C(O)NR_3R_4$ wherein $R_3$ and $R_4$ are as defined hereinbefore, $T_2$ represents a linear or branched $(C_1-C_6)$alkylene chain, $T'_2$ represents a linear or branched $(C_1-C_6)$alkylene chain optionally substituted with one ore more hydroxy groups, t represents an integer of from 0 to 2 inclusive, or Z represents a group selected from methylenedioxy or ethylenedioxy, $Q_1$ represents a group selected from an oxygen atom and an $NR_2$ group, wherein $R_2$ represents a group selected from a hydrogen atom and the groups linear or branched $(C_1-C_6)$alkyl, aryl, aryl-$(C_1-C_6)$alkyl in which the alkyl moiety may be linear or branched, cycloalkyl, cycloalkyl-$(C_1-C_6)$alkyl in which the alkyl moiety may be linear or branched, —$OR_3$, —$NR_3R_4$, —O-$T_2$-$NR_3R_4$, —$NR_3$-$T_2$-$NR_3R_4$, linear or branched $(C_1-C_6)$hydroxyalkylamino, di(($C_1-C_6$)hydroxyalkyl)amino in which the alkyl moieties may be linear or branched, —C(O)—$R_3$ and —NH—C(O)—$R_3$; or $R_2$ represents a linear or branched $(C_1-C_6)$alkylene chain substituted by one or more identical or different groups selected from halogen atoms and the groups cyano, nitro, —$OR_3$, —$NR_3R_4$, —$CO_2R_3$, —$C(O)R_3$, linear or branched $(C_1-C_6)$hydroxyalkylamino, di(($C_1-C_6$)hydroxyalkyl)amino in which the alkyl moieties may be linear or branched, and —C(O)—NHR$_3$, the groups R$_3$, R$_4$ and T$_2$ being as defined hereinbefore, Q$_2$ represents a group selected from an oxygen atom and an NR'$_2$ group wherein R'$_2$ represents a group selected from a hydrogen atom and the groups linear or branched (C$_1$–C$_6$)alkyl, aryl, aryl-(C$_1$–C$_6$)alkyl in which the alkyl moiety may be linear or branched, cycloalkyl, cycloalkyl-(C$_1$–C$_6$)alkyl in which the alkyl moiety may be linear or branched, —OR$_3$, —NR$_3$R$_4$, —O-T$_2$NR$_3$R$_4$, —NR$_3$-T$_2$-NR$_3$R$_4$, linear or branched (C$_1$–C$_6$)hydroxyalkylamino, di((C$_1$–C$_6$)hydroxyalkyl)amino in which the alkyl moieties may be linear or branched, —C(O)—R$_3$ and —NH—C(O)—R$_3$; or R'$_2$ represents a linear or branched. (C$_1$–C$_6$)alkylene chain substituted by one or more identical or different groups selected from halogen atoms and the groups cyano, nitro, —OR$_3$, —NR$_3$R$_4$, —CO$_2$R$_3$, —C(O)R$_3$, linear or branched (C$_1$–C$_6$)hydroxyalkylamino, di((C$_1$–C$_6$)-hydroxyalkyl)amino in which the alkyl moieties may be linear or branched, and —C(O)—NHR$_3$, the groups R$_3$, R$_4$ and T$_2$ being as defined hereinbefore, X$_1$ represents a group selected from a hydrogen atom and the groups hydroxy, linear or branched (C$_1$–C$_6$)alkoxy, mercapto, and linear or branched (C$_1$–C$_6$)alkylthio, Y$_1$ represents a hydrogen atom, or X$_1$ and Y$_1$, with the carbon atom carrying them, together form a carbonyl or thiocarbonyl group, X$_2$ represents a group selected from a hydrogen atom and the groups hydroxy, linear or branched (C$_1$–C$_6$)alkoxy, mercapto and linear or branched (C$_1$–C$_6$)alkylthio, Y$_2$ represents a hydrogen atom, or X$_2$ and Y$_2$, with the carbon atom carrying them, together form a carbonyl or thiocarbonyl group, X'$_1$ represents a group selected from a hydrogen atom and the groups hydroxy, linear or branched (C$_1$–C$_6$)alkoxy, mercapto and linear or branched (C$_1$–C$_6$)alkylthio, Y'$_1$ represents a hydrogen atom, or X'$_1$ and Y'$_1$, with the carbon atom carrying them, together form a carbonyl or thiocarbonyl group, X'$_2$ represents a group selected from a hydrogen atom and the groups hydroxy, linear or branched (C$_1$–C$_6$)alkoxy, mercapto and linear or branched (C$_1$–C$_6$)alkylthio, Y'$_2$ represents a hydrogen atom, or X'$_2$ and Y'$_2$, with the carbon atom carrying them, together form a carbonyl or thiocarbonyl group, R$_1$ represents a group selected from a hydrogen atom and a linear or branched (C$_1$–C$_6$)alkyl group that is optionally substituted by one or more groups selected from hydroxy, linear or branched (C$_1$–C$_6$)alkoxy, linear or branched (C$_1$–C$_6$)hydroxyalkoxy or NR$_3$R$_4$, the groups R$_3$ and R$_4$ being as defined hereinbefore; or R$_1$ represents a group of formula (a):

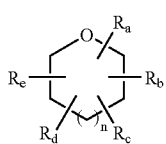

(a)

wherein:

R$_a$, R$_b$, R$_c$ and R$_d$, which may be identical or different, each represents, independently of the others, a bond or a group selected from a hydrogen atom, a halogen atom, and the groups hydroxy, linear or branched (C$_1$–C$_6$)alkoxy, aryloxy, aryl-(C$_1$–C$_6$)alkoxy in which the alkoxy moiety may be linear or branched, linear or branched (C$_1$–C$_6$)alkyl, aryl-(C$_1$–C$_6$)alkyl in which the alkyl moiety may be linear or branched, aryl, —NR$_3$R$_4$ wherein R$_3$ and R$_4$ are as defined hereinbefore, azido, —N=NR$_3$ (wherein R$_3$ is as defined hereinbefore), and —O—C(O)—R$_5$ wherein R$_5$ represents a linear or branched (C$_1$–C$_6$)alkyl group (optionally substituted by one or more groups selected from halogen, hydroxy, amino, linear or branched (C$_1$–C$_6$)-alkylamino, and di(C$_1$–C$_6$)alkylamino in which the alkyl moieties may be linear or branched); or R$_5$ represents aryl, aryl-(C$_1$–C$_6$)alkyl in which the alkyl moiety may be linear or branched, cycloalkyl or heterocycloalkyl, R$_e$ represents a methylene group (H$_2$C=) or a group of formula —U—R$_a$ wherein U$_1$ represents a single bond or a methylene group and R$_a$ is as defined hereinbefore, n is 0 or 1, it being understood that the group of formula (a) is bonded to the nitrogen atom by R$_a$, R$_b$, R$_c$, R$_d$ or R$_e$, to their enantiomers, diastereoisomers, and also to addition salts thereof with a pharmaceutically acceptable acid or base, with the proviso that the compounds of formula (I) are other than the following compounds:

3b,6a,6b,7-tetrahydro-1H-dipyrrolo[3,4-a:3,4-c]carbazole-1,3,4,6-(2H,3aH,5H)-tetrone;

5-ethyl-3b,6a,6b,7-tetrahydro-1H-dipyrrolo[3,4-a:3,4-c]carbazole-1,3,4,6-(2H,3aH,5H)-tetrone;

3b,6a,7,11c-tetrahydro-1H-dipyrrolo[3,4-a:3,4-c]carboazole-1,3,4,6-(2H,3aH,5H)-tetrone;

3b,6a,6b,7-tetrahydrofuro[3,4-a]pyrrolo[3,4-c]carbazole-1,3,4,6-(2H,3aH,5H)-tetrone;

wherein aryl is understood to mean a phenyl, naphthyl, dihydronaphthyl, tetrahydronaphthyl, indenyl or indanyl group, each of those groups optionally being substituted by one or more identical or different groups selected from halogen, linear or branched (C$_1$–C$_6$) alkyl, linear or branched (C$_1$–C$_6$)trihaloalkyl, hydroxy, linear or branched (C$_1$–C$_6$)alkoxy, and NR$_3$R$_4$, the groups R$_3$ and R$_4$ being as defined hereinbefore.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine etc.

Preferred compounds of the invention are those wherein X$_1$ and Y$_1$, with the carbon atom carrying them, together form a carbonyl group, X$_2$ and Y$_2$, with the carbon atom carrying them, together form a carbonyl group, X'$_1$ and Y'$_1$, with the carbon atom carrying them, together form a carbonyl group and X'$_2$ and Y'$_2$, with the carbon atom carrying them, together form a carbonyl group.

Advantageously, the Q$_1$ group preferred according to the invention is the group —NR$_2$ wherein R$_2$ is as defined for formula (I).

Advantageously, the Q$_2$ group preferred according to the invention is the group —NR'$_2$ wherein R'$_2$ is as defined for formula (I).

According to an advantageous embodiment, preferred compounds of the invention are compounds of formula (I) corresponding more especially to formula (IA):

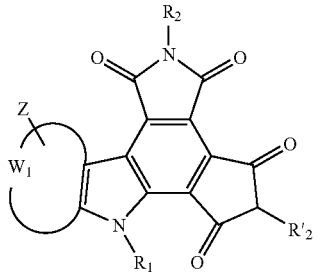

(IA)

wherein $R_1$, $R_2$, $R'_2$, $W_1$ and Z are as defined for formula (I).

According to a second advantageous embodiment, preferred compounds of the invention are compounds of formula (I) corresponding more especially to formula (IB):

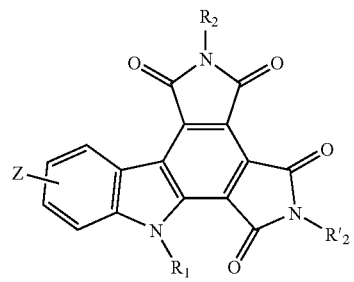

(IB)

wherein $R_1$, $R_2$, $R'_2$ and Z are as defined for formula (I).

According to a third advantageous embodiment, preferred compounds of the invention are compounds of formula (I) corresponding more especially to formula (IC):

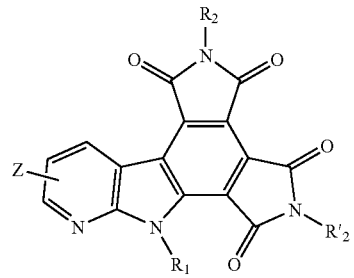

(IC)

wherein $R_1$, $R_2$, $R'_2$ and Z are as defined for formula (I).

According to a fourth advantageous embodiment, preferred compounds of the invention are compounds of formula (I) corresponding more especially to formula (ID):

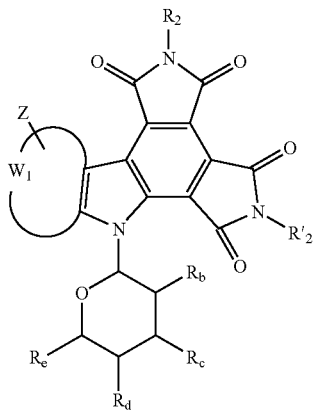

(ID)

wherein $R_2$, $R'_2$, $W_1$, Z, $R_b$, $R_c$, $R_d$ and $R_e$ are as defined for formula (I).

According to a fifth advantageous embodiment, preferred compounds of the invention are compounds of formula (I) corresponding more especially to formula (IE):

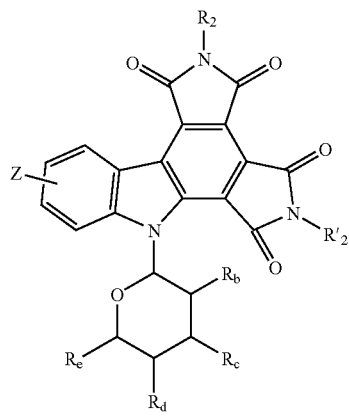

(IE)

wherein $R_2$, $R'_2$, Z, $R_b$, $R_c$, $R_d$ and $R_e$ are as defined for formula (I).

According to a sixth advantageous embodiment, preferred compounds of the invention are compounds of formula (I) corresponding more especially to formula (IF):

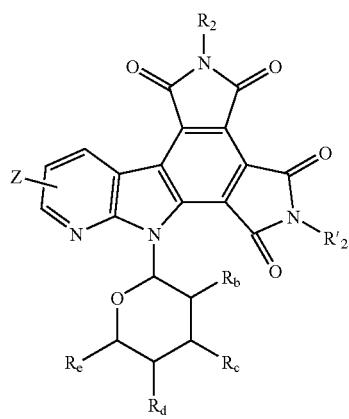

(IF)

wherein $R_2$, $R'_2$, Z, $R_b$, $R_c$, $R_d$ and $R_e$ are as defined for formula (I).

Preferably, the substituent Z preferred according to the invention is a group of formula U—V wherein U represents a single bond and V represents a group selected from a hydrogen atom, a halogen atom and the groups nitro, linear or branched $(C_1-C_6)$alkyl, hydroxy, linear or branched $(C_1-C_6)$alkoxy, aryl-$(C_1-C_6)$alkoxy in which the alkoxy moiety may be linear or branched, and $NR_3R_4$ wherein $R_3$ and $R_4$ each represents a hydrogen atom.

Even more preferably, the substituent Z preferred according to the invention is a group of formula U—V wherein U represents a single bond and V represents a group selected from a hydrogen atom, a halogen atom and the groups hydroxy and aryl-$(C_1-C_6)$alkoxy in which the alkoxy moiety may be linear or branched.

In an embodiment of interest, the group $R_1$ preferred according to the invention is a hydrogen atom, a linear or branched $(C_1-C_6)$alkyl group or a group of formula (a):

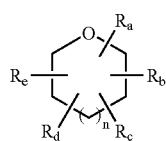
(a)

bonded to the nitrogen atom by Ra, wherein:
- $R_b$, $R_c$, and $R_d$ represent a hydroxy group, an aryl-$(C_1-C_6)$ alkoxy group in which the alkoxy moiety may be linear or branched, or a group —O—C(O)—$R_5$ wherein $R_5$ represents a linear or branched $(C_1-C_6)$alkyl group,
- $R_e$ represents a group of formula $U_1$—$R_a$ wherein $U_1$ represents a methylene group and $R_a$ has the same definitions as $R_b$, $R_c$ and $R_d$ and n is 0.

In an embodiment of even greater interest, the group $R_1$ preferred according to the invention is hydrogen.

In an embodiment of interest, the groups $R_2$ preferred according to the invention are hydrogen, linear or branched $(C_1-C_6)$alkyl, $OR_3$, $NR_3R_4$, and a linear or branched $(C_1-C_6)$alkylene chain substituted by an $OR_3$ or $NR_3R_4$ group wherein $R_3$ and $R_4$ are as defined for formula (I).

In an embodiment of even greater interest, the groups $R_2$ preferred according to the invention are hydrogen, linear or branched $(C_1-C_6)$alkyl, and a linear or branched $(C_1-C_6)$ alkylene chain substituted by an $NR_3R_4$ group wherein $R_3$ and $R_4$ are as defined for formula I.

In an embodiment of interest, the groups $R'_2$ preferred according to the invention are hydrogen, linear or branched $(C_1-C_6)$alkyl, and a linear or branched $(C_1-C_6)$alkylene chain substituted by an $NR_3R_4$ group wherein $R_3$ and $R_4$ are as defined for formula (I).

In an embodiment of interest, the group of formula (a) preferred according to the invention is the glucopyranosyl group of formula:

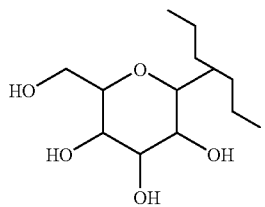

The following are preferred compounds according to the invention:
- 1H-dipyrrolo[3,4-a:3,4-c]carbazole-1,3,4,6-(2H,5H,7H)-tetrone,
- 2-methyl-1H-dipyrrolo[3,4-a:3,4-c]carbazole-1,3,4,6-(2H,5H,7H)-tetrone,
- 2,5-dimethyl-1H-dipyrrolo[3,4-a:3,4-c]carbazole-1,3,4,6-(2H,5H,7H)-tetrone,
- 2-[2-(diethylamino)ethyl]-5-methyl-1H-dipyrrolo[3,4-a:3,4-c]carbazole-1,3,4,6-(2H,5H,7H)-tetrone,
- 10-hydroxy-1H-dipyrrolo[3,4-a:3,4-c]carbazole-1,3,4,6-(2H,5H,7H)-tetrone The enantiomers, diastereoisomers, and addition salts with a pharmaceutically acceptable acid or base, of the preferred compounds form an integral part of the invention.

The present invention relates also to a process for the preparation of compounds of formula (I), which is characterised in that there is used as starting material a compound of formula (II):

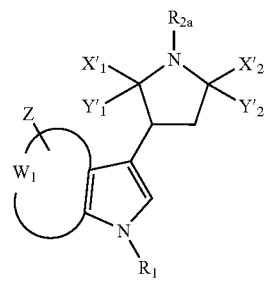
(II)

wherein $R_{2a}$ represents a hydrogen atom or a methyl group and $R_1$, $X'_1$, $Y'_1$, $X'_2$, $Y'_2$, $W_1$ and Z are as defined for formula (I), which is treated with 2,3-dichloro-5,6-dicyano-1,4-benzoquinone to yield a compound of formula (III):

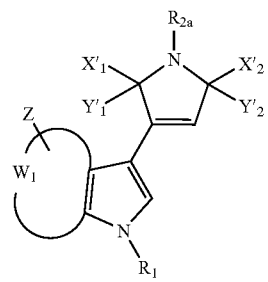
(III)

wherein $R_1$, $R_{2a}$, $X'_1$, $Y'_1$, $X'_2$, $Y'_2$, $W_1$ and Z are as defined hereinbefore, which compound of formula (III) is:
- either treated with aqueous sodium hydroxide solution and then placed in the presence of hydrochloric acid to yield a compound of formula (IV):

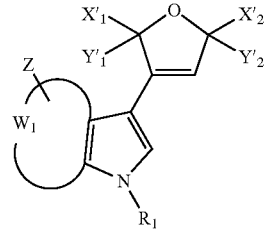
(IV)

wherein $R_1$, $X'_1$, $Y'_1$, $X'_2$, $Y'_2$, $W_1$ and Z are as defined hereinbefore, which compound of formula (IV) is treated with a compound of formula (V):

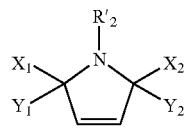
(V)

wherein R'$_2$, X$_1$, Y$_1$, X$_2$ and Y$_2$ are as defined for formula (I) to yield a compound of formula (I/a) and (I/b), a particular case of the compounds of formula (I):

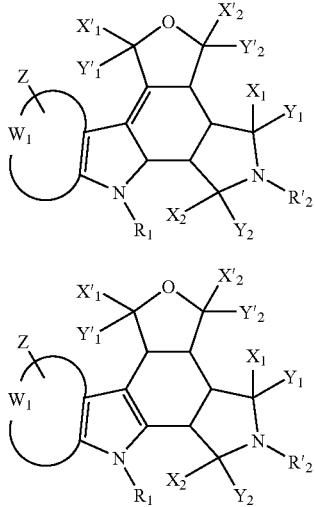

(I/a)

(I/b)

wherein R$_1$, R'$_2$, X$_1$, Y$_1$, X$_2$, Y$_2$, X'$_1$, Y'$_1$, X'$_2$, Y'$_2$, W$_1$ and Z are as defined hereinbefore, which compound(s) of formula (I/a) and/or (I/b) is(are) optionally subjected to the action of trifluoroacetic acid to yield a compound of formula (I/c), a particular case of the compounds of formula (I):

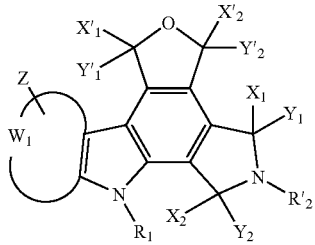

(I/c)

wherein R$_1$, R'$_2$, X$_1$, Y$_1$, X$_2$, Y$_2$, X'$_1$, Y'$_1$, X'$_2$, Y'$_2$, W$_1$ and Z are as defined hereinbefore, the totality of the compounds of formulae (I/a), (I/b) and (I/c) constituting the compounds of formula (I/d):

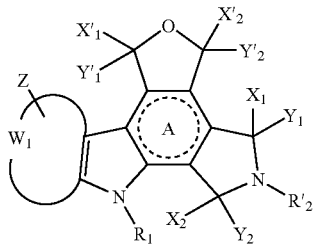

(I/d)

wherein A, R$_1$, R'$_2$, X$_1$, Y$_1$, X$_2$, Y$_2$, X'$_1$, Y'$_1$, X'$_2$, Y'$_2$, W$_1$ and Z are as defined hereinbefore, which compound of formula (I/d) is optionally subjected to the action of a compound of formula (VII):

$$R_{2b}-NH_2 \quad (VII)$$

wherein R$_{2b}$ has the same definition as R$_2$ in formula (I), with the exception of a hydrogen atom and a methyl group, to yield compounds of formula (I/e), a particular case of the compounds of formula (I):

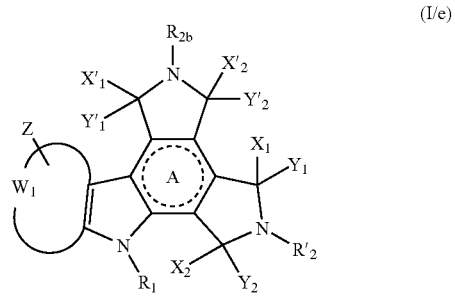

(I/e)

wherein A, R$_1$, R'$_2$, R$_{2b}$, X$_1$, Y$_1$, X$_2$, Y$_2$, X'$_1$, Y'$_1$, X'$_2$, Y'$_2$, W$_1$ and Z are as defined hereinbefore, or subjected in succession to the same reaction conditions as the compounds of formulae (IV), (I/a) and (I/b) to yield a compound of formula (I/f), a particular case of the compounds of formula (I):

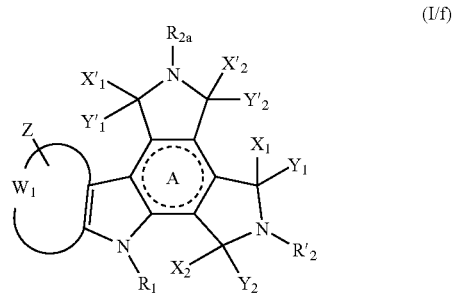

(I/f)

wherein A, R$_1$, R'$_2$, R$_{2a}$, X$_1$, Y$_1$, X$_2$, Y$_2$, X'$_1$, Y'$_1$, X'$_2$, Y'$_2$, W$_1$ and Z are as defined hereinbefore, the totality of the compounds (I/d), (I/e) and (I/f) constituting the compounds of formula (I/g):

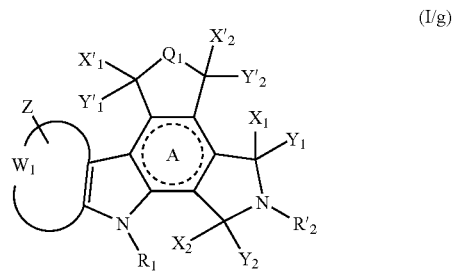

(I/g)

wherein A, R$_1$, R'$_2$, Q$_1$, X$_1$, Y$_1$, X$_2$, Y$_2$, X'$_1$, Y'$_1$, X'$_2$, Y'$_2$, W$_1$ and Z are as defined hereinbefore, which compound of formula (I/g), when R'$_2$ represents a hydrogen atom or a methyl group, is optionally subjected in succession to the same reactions conditions as the compound of formula (III) to yield a compound of formula (I/i), a particular case of the compounds of formula (I):

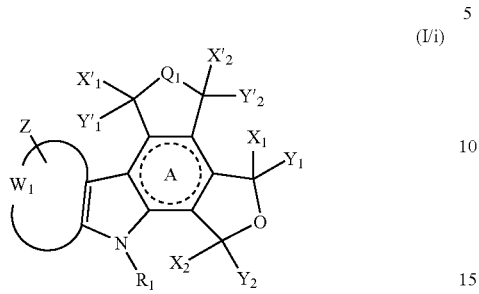

(I/i)

wherein A, $R_1$, $Q_1$, $X_1$, $Y_1$, $X_2$, $Y_2$, $X'_1$, $Y'_1$, $X'_2$, $Y'_2$, $W_1$ and Z are as defined hereinbefore, which compound of formula (I/i) is optionally subjected to the action of a compound (VIII):

$$R'_{2b}-NH_2 \qquad (VIII)$$

wherein $R'_{2b}$ has the same definition as $R'_2$ in formula (I), with the exception of the definitions hydrogen atom and methyl group, to yield compounds of formula (I/j), a particular case of the compounds of formula (I):

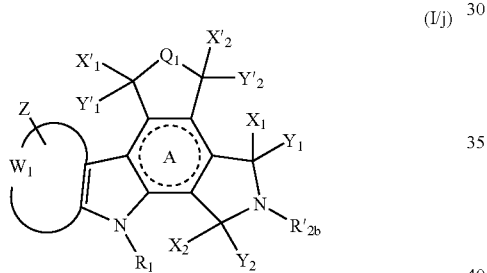

(I/j)

wherein A, $R_1$, $R'_{2b}$, $Q_1$, $X_1$, $Y_1$, $X_2$, $Y_2$, $X'_1$, $Y'_1$, $X'_2$, $Y'_2$, $W_1$ and Z are as defined hereinbefore, the compounds of formulae (I/a) to (I/j) constituting the totality of the compounds of formula (I), which, if appropriate, are purified according to conventional purification techniques, may, if desired, be separated into their different isomers according to a conventional separation technique, the substituents $R_a$, $R_b$, $R_c$, $R_d$ and $R_e$ of which may be modified according to conventional methods of organic synthesis used in the field of sugar chemistry, and which compounds, if desired, are converted into addition salts with a pharmaceutically acceptable acid or base.

The compounds of formula (II) may advantageously be obtained starting from a compound of formula (A):

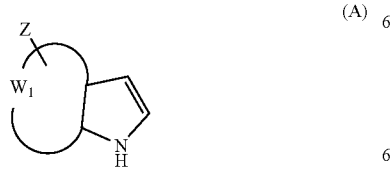

(A)

wherein $W_1$ and Z are as defined for formula (I), which is reacted:

either with a compound of formula (B):

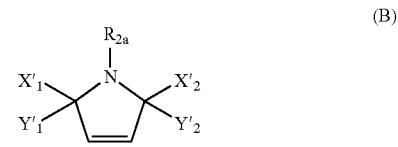

(B)

wherein $R_{2a}$, $X'_1$, $Y'_1$, $X'_2$ and $Y'_2$ are as defined hereinbefore, to yield a compound of formula (C):

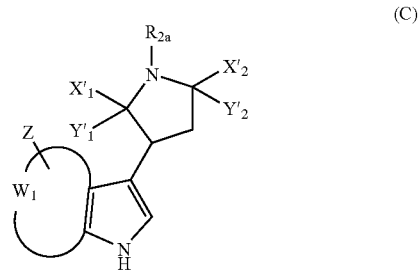

(C)

wherein $R_{2a}$, $X'_1$, $Y'_1$, $X'_2$, $Y'_2$, $W_1$ and Z are as defined hereinbefore, which compound of formula (C) is optionally subjected to the action of a compound of formula (IX):

$$R_{1a}-G \qquad (IX)$$

wherein G represents a hydroxy group or a leaving group and $R_{1a}$, which is other than a hydrogen atom, has the same definition as $R_1$ in formula (I), to yield a compound of formula (D):

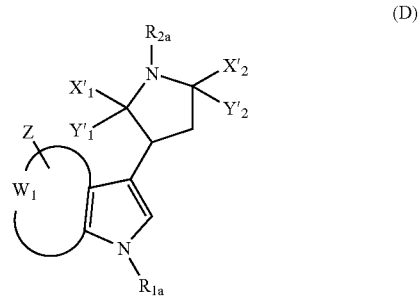

(D)

wherein $R_{1a}$, $R_{2a}$, $X'_1$, $Y'_1$, $X'_2$, $Y'_2$, $W_1$ and Z are as defined hereinbefore, the compounds of formulae (C) and (D) constituting the totality of the compounds of formula (II), or with a compound of formula (E) in the presence of alkylmagnesium halide:

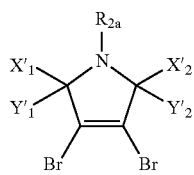
(E)

wherein $R_{2a}$, $X'_1$, $Y'_1$, $X'_2$ and $Y'_2$ are as defined hereinbefore, to yield a compound of formula (F):

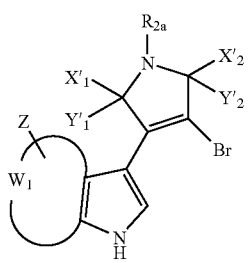
(F)

wherein $R_{1a}$, $R_{2a}$, $X'_1$, $Y'_1$, $X'_2$, $Y'_2$, $W_1$ and Z are as defined hereinbefore, which compound of formula (F) is optionally subjected to the same reaction conditions as the compound of formula (C), to yield a compound of formula (G):

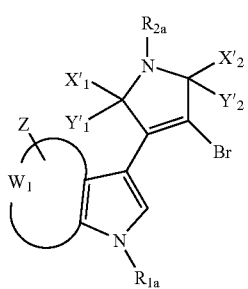
(G)

wherein $R_{1a}$, $R_{2a}$, $X'_1$, $Y'_1$, $X'_2$, $Y'_2$, $W_1$ and Z are as defined hereinbefore, which compound of formula (G) is hydrogenated according to conventional methods of organic synthesis to yield a compound of formula (II).

The compounds of formulae (V), (VII), (VIII), (IX), (A), (B) and (E) are either commercially available products or are products obtained according to conventional methods of organic synthesis well known to the person skilled in the art.

The compounds of formula (I) exhibit anti-tumour properties that are of particular interest. The characteristic properties of those compounds allow them to be used therapeutically as anti-tumour agents.

The compounds of the invention may also be used in therapeutic association with another anti-cancer agent, such as, for example, paclitaxel, tamoxifen and derivatives thereof, cisplatin and analogues thereof, irinotecan and metabolites thereof, various alkylating agents, the chief of which is cyclophosphamide, etoposide, vinca alkaloids, doxorubicin and other anthracyclins, and nitrosoureas.

The present invention relates also to pharmaceutical compositions comprising as active ingredient at least one compound of formula (I), optical isomers thereof, or an addition salt thereof with a pharmaceutically acceptable acid or base, on its own or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous), per- or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, eye drops and nose drops etc.

By virtue of the pharmacological properties characteristic of the compounds of formula (I), the pharmaceutical compositions comprising the said compounds of formula (I) as active ingredient are accordingly especially useful in the treatment of cancers.

The useful dosage varies according to the age and weight of the patient, the administration route, the nature and the severity of the disorder, and the administration of any associated treatments, and ranges from 1 mg to 500 mg per day in one or more administrations.

The Examples that follow illustrate the invention but do not limit in in any way. The starting materials employed are known products or products prepared according to known procedures.

The structures of the compounds described in the Examples were determined according to customary spectrophotometric techniques (infrared, nuclear magnetic resonance, mass spectrometry, . . . ).

PREPARATION A 3b,6a,6b,7-tetrahydro-1H-dipyrrolo[3,4-a:3,4-c]carbazole-1,3,4,6(2H,3aH,5H)-tetrone Step A: 3-(1H-indol-3-yl)-2,5-pyrrolidinedione The expected product is obtained in accordance with the process described by J. Bergman et al. (Tetrahedron, 1999, 55, pp. 2363–2370).

Step B: 3-(1H-indol-3-yl)-1H-pyrrole-2,5-dione

The expected product is obtained in accordance with the process described by J. Bergman et al. (Tetrahedron, 1999, 55, pp. 2363–2370).

Step C: 3b,6a,6b,7-tetrahydro-1H-dipyrrolo[3,4-a:3,4-c]carbazole-1,3,4,6(2H,3aH,5H)-tetrone The expected product is obtained in accordance with the process described by J. Bergman et al. (J. Chem. Soc., Perkin Trans. I, 2000. pp. 2615–2621).

PREPARATION B 3-(1H-indol-3-yl)-1-methyl-1H-pyrrole-2,5-dione

Step A: 3-(1H-indol-3-yl)-1-methyl-2,5-pyrrolidinedione

The expected product is obtained in accordance with the process described by J. Bergman et al. (Tetrahedron, 1999, 55, pp. 2363–2370).

Step B: 3-(1H-indol-3-yl)-1-methyl-1H-pyrrole-2,5-dione

The expected product is obtained in accordance with the process described by J. Bergman et al. (Tetrahedron, 1999, 55, pp. 2363–2370).

PREPARATION C

3-[5-(benzyloxy)-1H-indol-3-yl]-1-methyl-1H-pyrrole-2,5-dione

Step A: 3-[5-(benzyloxy)-1H-indol-3-yl]-1-methy-2,5-pyrrolidinedione

A mixture of 5-benzyloxy-indole (8 mmol) and N-methylmaleimide (8 mmol) in 8 ml of acetic acid is refluxed for 48 hours. The acetic acid is evaporated off. Purification by chromatography on silica gel (ethyl acetate/cyclohexane: 2/8 to 7/3) allows the expected product to be obtained.

Melting point: 49–53° C.
IR (KBr): $v_{C=O}$=1690, 1700 cm$^{-1}$; $v_{NH}$=3300–3500 cm$^{-1}$.
Mass spectrum (FAB): 335.14 [M+H$^+$].

Step B: 3-[5-(benzyloxy)-1H-indol-3-yl]-1-methyl-1H-pyrrole-2,5-dione

A solution of 2,3-dichloro-5,6-dicyano-1,4-benzoquinone (2 mmol) in 20 ml of dioxane is slowly added to a solution of the compound obtained in the above Step (2 mmol) in 20 ml of dioxane. The reaction mixture is stirred overnight at ambient temperature. After filtration, followed by removal of the dioxane by evaporation, the reaction mixture is taken up in isopropanol for recrystallisation. The expected product is obtained by filtration and washing with isopropane the precipitate that has formed.

Melting point: 176–182° C.
IR (KBr): $v_{C=O}$=1690, 1700 cm$^{-1}$; $v_{NH}$=3300–3440 cm$^{-1}$.
Mass spectrum (FAB): 333.12 [M+H$^+$].

PREPARATION D 3-(1H-indol-3-yl)-2,5-furandione

A mixture of the compound of Preparation B (0.884 mmol) and sodium hydroxde pellets (12.5 mmol) in 100 ml of distilled water is refluxed for 2 hours. After cooling the reaction mixture, concentrated hydrochloric acid is added dropwise until a precipitate is formed. The expected product is isolated by filtration of the precipitate.

Melting point: 210–214° C.
IR (KBr): $v_{C=O}$=1740, 1800 cm$^{-1}$; $v_{NH}$=3320 cm$^{-1}$.

PREPARATION E 3-(1H-pyrrolo[2,3-b]pyridin-3-yl)-1H-pyrrole-2,5-dione

Step A: 3-bromo-4-(1H-pyrrolo[2,3-b]pyridin-3-yl)-1H-pyrrole-2,5-dione

A solution of ethylmagnesium bromide is prepared from magnesium (12.7 mmol) suspended in bromoethane (12.7 mmol) and dry tetrahydrofuran (5 ml). The solution is stirred for 1 hour at ambient temperature and then 7-azaindole (12.7 mmol), dissolved in 40 ml of anhydrous toluene is added dropwise. After 1 hour 30 minutes' stirring at ambient temperature, a solution of 2,3-dibromomaleimide (3.53 mmol) in 40 ml of anhydrous toluene is added dropwise. After 20 minutes, 60 ml of dry dichloromethane are added, and then the reaction mixture is stirred for 75 hours at 40° C. and subsequently hydrolysed with a saturated aqueous ammonium chloride solution. The organic product is extracted with ethyl acetate, and then the combined organic phases are dried over magnesium sulphate and filtered. After removal of the solvent by evaporation, and purification of the residue by chromatography on silica gel (cyclohexane/ethyl acetate: 3/2), the expected product is isolated.

Step B: 3-(1H-pyrrolol[2,3-b]pyridin-3-yl)-2,5-pyrrolidinedione

A mixture of the compound obtained in the above Step (0.327 mmol) and a catalytic amount of 10% palladium-on-carbon in methanol (40 ml) is hydrogenated at one atmosphere for 24 hours. The mixture is filtered over Celite and the expected product is obtained after purification of the residue by chromatography on silica gel using ethyl acetate as eluant.

Step C: 3-(1H-pyrrolo[2,3-b]pyridin-3-yl)-1H-pyrrole-2,5-dione

The expected product is obtained in accordance with the procedure described in Step B of Preparation C, starting from the compound of the above Step.

PREPARATION F 1-methyl-3-[1-(2,3,4,6-tetra-O-acetyl-β-D-glueopyranosyl)-1H-pyrrolo[2,3-b]pyridin-3-yl]-1H-pyrrole-2,5-dione Step A: 3-bromo-1-methyl-4-(1H-pyrrolo[2,3-b]pyridin-3-yl)-1H-pyrrole-2,5-dione The expected product is obtained in accordance with the procedure described in Step A of Preparation E, using N-methyl-2,3-dibromomaleimide as substrate.

Melting point: 158° C.

Step B: 3-bromo-1-methyl-4-[1-(2,3,4,6-tetra-O-acetyl-β-D-glucopyranosyl)-1H-pyrrolo[2,3-b]pyridin-3-yl]-1-H-pyrrole-2,5-dione 2,3,4,6-Tetra-O-acetylglucopyranose (1.95 mmol) and triphenylphosphine (1.95 mmol) are added dropwise to a solution of the compound of the above Step (0.927 mmol) dissolved in 40 ml of dry tetrahydrofuran. The temperature is slowly brought back to ambient temperature, and then the reacton mixture is stirred for a further 15 hours. Following hydrolysis, the organic product is extracted with ethyl acetate. The organic phases are combined, dried over magnesium sulphate and filtered, and the solvent is evaporated off. The expected product is obtained after purification by chromatography on silica gel.

Step C: 1-methyl-3-[1-(2,3,4,6-tetra-O-acetyl-β-D-glucopyranosyl)-1H-pyrrolo[2,3-b]pyridin-3-yl]-2,5-pyrrolidinedione The expected product is obtained in accordance with the procedure described in Step B of Preparation E, starting from the compound of the above Step.

Step D: 1-methyl-3-[1-(2,3,4,6-tetra-O-acetyl-β-D-glucopyranosyl)-1H-pyrrolo[2,3-b]pyridin-3-yl]-1H-pyrrole-2,5-dione The expected product is obtained in accordance with the procedure described in Step B of Preparation C, starting from the compound of the above Step.

PREPARATION G 1-methyl-3-(1H-pyrrolo[2,3-b]pyridin-3-yl)-1H-pyrrole-2,5-dione Step A: 1-methyl-3-(1H-pyrrolo[2,3-b]pyridin-3-yl)-2,5-pyrrolidinedione A mixture of the compound obtained in Step A of Preparation F (0.65 mmol) and 10% palladium-on-carbon (20 mg) in methanol (40 ml) is hydrogenated at 1 atmosphere for 3.5 hours. The mixture is filtered over Celite. The filtrate is evaporated off and the expected product is obtained after purification of the residue by flash chromatography on silica gel (AcOEt then AcOEt/MeOH 9:1).

Melting point: 199–202° C.

IR (KBr): $v_{C=O}$=1690, 1770 cm$^{-1}$; $v_{NH}$=3250–3500 cm$^{-1}$.

Step B: 1-methyl-3-(1H-pyrrolo[2,3-b]pyridin-3-yl)-1H-pyrrole-2,5-dione

The expected product is obtained in accordance with the procedure described in Step B of Preparation C, starting from the compound of the above Step.

Melting point: >250° C.

IR (KBr): $v_{C=O}$=1700, 1760 cm$^{-1}$; $v_{NH}$=3300–3600 cm$^{-1}$.

PREPARATION H

3-[5-(benzyloxy)-1H-indol-3-yl]-1H-pyrrole-2,5-dione

Step A: 3-[5-(benzyloxy)-1H-indol-3-yl]-2,5-pyrrolidinedione

The expected product is obtained in accordance with the procedure described in Step A of Preparation C, with the replacement of N-methylmaleimide by maleimide.

Melting point: 175° C.

IR (KBr) $v_{C=O}$=1690, 1780 cm$^{-1}$; $v_{NH}$=3210–3320 cm$^{-1}$.

Step B: 3-[5-(benzyloxy)-1H-indol-3-yl]-1H-pyrrole-2,5-dione

The expected product is obtained in accordance with the procedure described in Step B of Preparation C, starting from the compound of the above Step.

Melting point: 211° C.

IR (KBr): $v_{C=C}$=1600 cm$^{-1}$; $v_{C=O}$=1705, 1755 cm$^{-1}$; $v_{NH}$=3150–3450 cm$^{-1}$.

PREPARATION I 3-(5-bromo-1H-indol-3-yl)-1H-pyrrole-2,5-dione

Step A: 3-(5-bromo-1H-indol-3-yl)-2,5-pyrrolidinedione

The expected product is obtained in accordance with the procedure described in Step A of Preparation C, with the replacement of N-methylmaleimide by maleimide and of 5-benzyloxy-indole by 5-bromo-indole.

Melting point: 208–215° C.

IR (KBr): $v_{C=O}$=1700, 1755 cm$^{-1}$; $v_{NH}$=3450 cm$^{-1}$.

Step B: 3-(5-bromo-1H-indol-3-yl)-1H-pyrrole-2,5-dione

The expected product is obtained in accordance with the procedure described in Step B of Preparation C, starting from the compound of the above Step.

Melting point: 268° C.

IR (KBr): $v_{C=C}$=1595 cm$^{-1}$; $v_{C=O}$=1705, 1750 cm$^{-1}$; $v_{NH}$=3200–3340 cm$^{-1}$.

PREPARATION J 3-(5-chloro-1H-indol-3-yl)-1H-pyrrole-2,5-dione

Step A: 3-(5-chloro-1H-indol-3-yl)-2,5-pyrrolidinedione

The expected product is obtained in accordance with the procedure described in Step A of Preparation I, with the replacement of 5-bromo-indole by 5-chloro-indole.

IR (KBr): $v_{C=O}$=1700, 1780 cm$^{-1}$; $v_{NH}$=3200–3500 cm$^{-1}$.

Step B: 3-(5-chloro-1H-indol-3-yl)-1H-pyrrole-2,5-dione

The expected product is obtained in accordance with the procedure described in Step B of Preparation C, starting from the compound of the above Step.

Melting point: 254–264° C.

IR (KBr): $v_{C=C}$=1605 cm$^{-1}$; $v_{C=O}$=1710, 1750 cm$^{-1}$; $v_{NH}$=3100–3350 cm$^{-1}$.

PREPARATION K 3-(5-fluoro-1H-indol-3-yl)-1H-pyrrole-2,5-dione

Step A: 3-(5-fluoro-1H-indol-3-yl)-2,5-pyrrolidinedione

The expected product is obtained in accordance with the procedure described in Step A of Preparation I, with the replacement of 5-bromo-indole by 5-fluoro-indole.

Melting point: 190–195° C.

IR (KBr): $v_{C=C}$=1690, 1775 cm$^{-1}$; $v_{NH}$=3360 cm$^{-1}$.

Step B: 3-(5-fluoro-1H-indol-3-yl)-1H-pyrrole-2,5-dione

The expected product is obtained in accordance with the procedure described in Step B of Preparation C, starting from the compound of the above Step.

Melting point: 255–265° C.

IR (KBr): $v_{C=C}$=1605 cm$^{-1}$; $v_{C=O}$=1720, 1750 cm$^{-1}$; $v_{NH}$=3150–3350 cm$^{-1}$.

PREPARATION L 3-(5-hydroxy-1H-indol-3-yl)-1H-pyrrole-2,5-dione

Step A: 3-(5-hydroxy-1H-indol-3-yl)-2,5-pyrrolidinedione

10% palladium-on-carbon (135 mg) is added to a solution of the compound of Step A of Preparation H (450 mg) in dry methanol (90 ml). After having purged in vacuo for 20 minutes, the reaction mixture is placed under a hydrogen atmosphere (1 atm) for 3 hours. Following filtration over Celite and evaporation of the filtrate, the expected product is obtained.

IR (film): $v_{C=C}$=1700 cm$^{-1}$; $v_{NH,OH}$=3000–3700 cm$^{-1}$.

Step B: 3-(5-hydroxy-1H-indol-3-yl)-1H-pyrrole-2,5-dione

The expected product is obtained in accordance with the procedure described in Step B of Preparation C, starting from the compound of the above Step.

Melting point: 292–298° C.

IR (KBr) $v_{C=C}$=1610 cm$^{-1}$; $v_{C=O}$=1690, 1760 cm$^{-1}$; $v_{NH,OH}$=3260, 3370, 3430 cm$^{-1}$.

PREPARATION M

3-[1-(2,3,4,6-tetra-O-benzyl-β-D-glueopyranosyl)-1H-indol-3-yl]-1H-pyrrole-2,5-dione Step A: 3-bromo-4-(1H-indol-3-yl)-1-methyl-1H-pyrrole-2,5-dione A solution of 1.445 g of indole dissolved in 29 ml of dry tetrahydrofliran is brought to from −20 to −10° C. under argon, and then 26 ml of LiHMDS (1M in hexane) are added dropwise in the course of 15 minutes. After 45 minutes at −10° C., the solution is diluted with an additional 15 ml of tetrahydrofuran and a solution of 2 g of N-methyl-2,3-dibromomaleimide dissolved in 17 ml of tetrahydrofuran is added dropwise in the course of 30 minutes. After 15 minutes at −10° C. and 15 minutes at 0° C., the reaction is stopped by the addition, at 0° C., of 50 ml of a 0.3N hydrochloric acid solution. The reaction mixture is extracted with ethyl acetate, and the organic phases are washed with a saturated NaCl solution, dried over MgSO₄ and then evaporated under reduced pressure. The desired product is precipitated using methanol.

Melting point=167–168° C.

Step B: 3-bromo-1-methyl-4-[1-(2,3,4,6-tetra-O-benzyl-β-D-glucopyranosyl)-1-H-indol-3-yl]-1H-pyrrole-2,5-dione A solution of the compound of the above Step A, PPh₃ (3 equiv.) and 2,3,4,6-tetra-O-benzyl-D-glucopyranosyl (3 equiv.) in dry THF is cooled to −78° C. DIAD (3 equiv.) is then added dropwise. The reaction mixture is stirred for 4 hours, while allowing to warm up again to ambient temperature. A 0.2M solution of HCl is poured in and the mixture is extracted with ethyl acetate. The organic phase is washed in succession with a saturated aqueous NaHCO₃ solution and with water and then dried over MgSO₄. After filtration and removal of the solvent by evaporation, and chromatography on silica gel (toluene/ethyl acetate: 50/1), the expected product is obtained.

Melting point: 55° C.

IR (KBr): $v_{C=C}$=1640 cm$^{-1}$; $v_{C=O}$=1710, 1770 cm$^{-1}$; $v_{NH,OH}$=3200–3600 cm$^{-1}$.

Step C: 1-methyl-3-[1-(2,3,4,6-tetra-O-benzyl-β-D-glucopyranosyl)-1H-indol-3-yl]2,5-pyrrolidinedione A solution of the compound of the above Step B in methanol and dry THF is hydrogenated (1 atm.) for 3 hours in the presence of 10% palladium-on-carbon and pyridine (0.5 equiv.). Following filtration over Celite and evaporation of the filtrate, and chromatography on silica gel (cyclohexane/ethyl acetate), the expected product is obtained.

Step D: 1-methyl-3-[1-(2,3,4,6-tetra-O-benzyl-β-D-glucopyranosyl)-1H-indol-3-yl]-1H-pyrrole-2,5-dione The expected product is obtained in accordance with the procedure described in Step B of Preparation C, starting from the compound of the above Step.

Step E: 3-[1-(2,3,4,6-tetra-O-benzyl-β-D-glucopyranosyl)-1H-indol-3-yl]-1H-pyrrole-2,5-dione A mixture of the compound of the above Step D and NaOH in distilled water is heated at reflux for 2 hours. After cooling, concentrated hydrochloric acid is poured in dropwise until a yellow precipitate is formed. The yellow solid is filtered off over a frit and washed with water, yielding the desired anhydride, which is then treated with a solution of ammonium hydroxide in THF to yield the expected compound.

PREPARATION N

3-{[1-(2,3,4,6-tetra-O-benzyl-β-D-glucopyranosyl)]-1H-pyrrolo[2,3-b]pyridin-3-yl}-1H-pyrrole-2,5-dione Step A: 3-bromo-1-methyl-4-[1-(2,3,4,6-tetra-O-benzyl-β-D-glucopyranosyl)-1H-pyrrolo[2,3-b]pyridin-3-yl]-1H-pyrrole-2,5-dione 2,3,4,6-O-benzylglucopyranosyl (264 mg) and triphenylphosphine (128 mg) are added to a solution of the compound of Step A of Preparation G (50 mg) dissolved in 4 ml of dry THF. The reaction mixture is cooled to −78° C., and then DIAD (97 μl) is added dropwise. The temperature is slowly brought back to ambient temperature and then the reaction mixture is stirred for a further 15 hours. Following hydrolysis (40 ml of water), the organic product is extracted with ethyl acetate (3×150 ml). The organic phases are combined, dried over magnesium sulphate and filtered, and the solvent is evaporated off. Purification by chromatography on silica gel (cyclohexane/ethyl acetate: 8/2 to 7/3) allows the expected product to be isolated.

IR (KBr): $v_{C=O}$=1710, 1740, 1760 cm$^{-1}$.

Step B: 1-methyl-3-[1-(2,3,4,6-tetra-O-benzyl-β-D-glucopyranosyl)-1H-pyrrolo[2,3-b]pyridin-3-yl]-2,5-pyrrolidinedione NaHCO₃ (66 mg) and 10% Pd/C (65 mg) are added to a suspension of the compound of the above Step A (65 mg) in 10 ml of ethyl acetate. The mixture is placed under a hydrogen atmosphere (1 bar) at ambient temperature for 24 hours. Filtration over Celite allows the catalyst to be removed and the filtrate is evaporated under reduced pressure. Purification by flash chromatography on silica gel (cyclohexane/ethyl acetate: 8/2 to 7/3) allows the expected product to be isolated.

IR (KBr): $v_{C=O}$=1710–1750 cm$^{-1}$.

Step C: 1-methyl-3-{[1-(2,3,4,6-tetra-O-benzyl-β-D-glucopyranosyl)]-1H-pyrrolo[2,3-b]pyridin-3-yl}-1H-pyrrole-2,5-dione The expected product is obtained in accordance with the procedure described in Step B of Preparation C, starting from the compound of the above Step.

Step D: 3-{[1-(2,3,4,6-tetra-O-benzyl-β-D-glucopyranosyl)]-1H-pyrrolo[2,3-pyridin-3-yl}-2,5-furandione NaOH pellets (14 mmol) and THF are added to a suspension of the compound of the above Step C (1 mmol) in water. The mixture is stirred at ambient temperature for 2 hours, and is then acidified to pH 1 by the addition of concentrated hydrochloric acid. After stirring for 30 minutes, the organic product is extracted with ethyl acetate (3×150 ml). The organic phases are combined, dried over magnesium sulphate and filtered, and the solvent is evaporated off. Purification by chromatography on silica gel allows the expected product to be isolated.

Step E: 3-{[1-(2,3,4,6-tetra-O-benzyl-β-D-glucopyranosyl)]-1H-pyrrolo[2,3-b]-pyridin-3-yl}-1H-pyrrole-2,5-dione In a sealed tube, a solution of the compound of the above Step D in THF is added to a solution of THF saturated with NH₃. The reaction mixture is stirred at 80° C. for 18 hours. After cooling, the mixture is poured into water and extracted repeatedly with ethyl acetate. The organic phases are combined, dried over magnesium sulphate and filtered, and the solvent is evaporated off. Purification by chromatography on silica gel allows the expected product to be isolated.

The compounds of Preparations O to AP are obtained according to the procedure of Preparation C, starting from the appropriate indoles and with the replacement of N-methylmaleimide by maleimide.

PREPARATION O 3-(5-amino-1H-indol-3-yl)-1H-pyrrole-2,5-dione

PREPARATION P 3-(4-amino-1H-indol-3-yl)-1H-pyrrole-2,5-dione

PREPARATION Q 3-(5,6-dimethoxy-1H-indol-3-yl)-1H-pyrrole-2,5-dione

PREPARATION R 3-(4-nitro-1H-indol-3-yl)-1H-pyrrole-2,5-dione

PREPARATION S 3-(4-fluoro-1H-indol-3-yl)-1H-pyrrole-2,5-dione

PREPARATION T 3-(6-fluoro-1H-indol-3-yl)-1H-pyrrole-2,5-dione

PREPARATION U 3-(4-hydroxy-1H-indol-3-yl)-1H-pyrrole-2,5-dione

PREPARATION V 3-(5-hydroxy-1H-indol-3-yl)-1H-pyrrole-2,5-dione

PREPARATION W 3-(4-methoxy-1H-indol-3-yl)-1H-pyrrole-2,5-dione

PREPARATION X 3-(5-methoxy-1H-indol-3-yl)-1H-pyrrole-2,5-dione

PREPARATION Y 3-(6-methoxy-1H-indol-3-yl)-1H-pyrrole-2,5-dione

PREPARATION Z 3-(7-methoxy-1H-indol-3-yl)-1H-pyrrole-2,5-dione

PREPARATION AA 3-(4-methyl-1H-indol-3-yl)-1H-pyrrole-2,5-dione

PREPARATION AB 3-(5-methyl-1H-indol-3-yl)-1H-pyrrole-2,5-dione

PREPARATION AC 3-(6-methyl-1H-indol-3-yl)-1H-pyrrole-2,5-dione

PREPARATION AD 3-(7-methyl-1H-indol-3-yl)-1H-pyrrole-2,5-dione

PREPARATION AE 3-(4-chloro-1H-indol-3-yl)-1H-pyrrole-2,5-dione

PREPARATION AF 3-(5-chloro-1H-indol-3-yl)-1H-pyrrole-2,5-dione

PREPARATION AG 3-(6-chloro-1H-indol-3-yl)-1H-pyrrole-2,5-dione

PREPARATION AH 3-(7-chloro-1H-indol-3-yl)-1H-pyrrole-2,5-dione

PREPARATION AI 3-(4-bromo-1H-indol-3-yl)-1H-pyrrole-2,5-dione

PREPARATION AJ 3-(6-bromo-1H-indol-3-yl)-1H-pyrrole-2,5-dione

PREPARATION AK 3-(7-bromo-1H-indol-3-yl)-1H-pyrrole-2,5-dione

PREPARATION AL 3-(5-methoxy-4-methyl-1H-indol-3-yl)-1H-pyrrole-2,5-dione

PREPARATION AM

3-[(7-(benzyloxy)-1H-indol-3-yl]-1H-pyrrole-2,5-dione

PREPARATION AN

3-[6-(benzyloxy)-1H-indol-3-yl]-1H-pyrrole-2,5-dione

PREPARATION AO

3-[5-(benzyloxy)-6-methoxy-1H-indol-3-yl]-1H-pyrrole-2,5-dione

PREPARATION AP 3-(1-methyl-1H-indol-3-yl]-1H-pyrrole-2,5-dione

EXAMPLE 1

1H-dipyrrolo[3,4-a:3,4-c]carbazole-1,3,4,6(2H,5H,7H)-tetrone

The compound of Preparation A (0.388 mmol) is heated at reflux for 24 hours in 24 ml of dioxane in the presence of trifluoroacetic acid (400 μl). After removal of the solvent by evaporation, the crystals are taken up in ethyl acetate and washed with a saturated sodium hydrogen carbonate solution and a saturated sodium chloride solution. The expected product is obtained by filtration of the crystals over a frit.

Melting point: >300° C.

IR (KBr): $v_{C=O}$=1690, 1730, 1745, 1780 cm$^{-1}$; $v_{NH}$=3280–3380 cm$^{1}$.

Mass spectrometry (FAB): 306.05 [M+H$^+$].

EXAMPLE 2

2,5-dimethyl-1H-dipyrrolo[3,4-a:3,4-c]carbazole-1, 3,4,6(2H,5H,7H)-tetrone

A mixture of the compound of Preparation B (1 mmol) and N-methylmaleimide (1.10 mmol) in 17 ml of para-xylene is refluxed for 24 hours. After cooling, the yellow precipitate is filtered off and then washed with para-xylene. Chromatography on a silica column (ethyl acetate/cyclohexane: 1/1; ethyl acetate; ethyl acetate/methanol: 98/2) allows a mixture of isomers to be obtained which is heated at reflux for 84 hours in 25 ml of dioxane in the presence of trifluoroacetic acid. After removal of the solvent by evaporation, the crystals are taken up in ethyl acetate and washed with a saturated sodium hydrogen carbonate solution and a saturated sodium chloride solution. The expected product is obtained by filtration of the crystals over a frit.

Melting point: >300° C.

IR (KBr): $v_{C=O}$1695, 1720 cm$^{-1}$; $v_{NH}$=3410 cm$^{-1}$.

Mass spectrometry (FAB): 334.08 [M+H$^+$].

EXAMPLE 3

2-methyl-1H-dipyrrolo[3,4-a:3,4-c]carbazole-1,3,4,6 (2H,5H,7H)-tetrone

The expected product is obtained in accordance with the procedure described in Example 2, starting from the compound of Preparation B and maleimide.

Melting point: >300° C.

IR (KBr): $v_{C=O}$=1710, 1720, 1760, 1780 cm$^{-1}$; $v_{NH}$=3260–3395 cm$^{-1}$.

Mass spectrometry (FAB): 320.06 [M+H$^+$].

EXAMPLE 4

10-(benzyloxy)-2,5-dimethyl-1H-dipyrrolo[3,4-a:3, 4-c]carbazole-1,3,4,6(2H,5H,7H)-tetrone The expected product is obtained in accordance with the procedure described in Example 2, starting from the compound of Preparation C and N-methylmaleimide.

Melting point: >300° C.

IR (KBr): $v_{C=O}$=1700, 1720, 1775 cm$^{-1}$; $v_{NH}$=3480 cm$^{-1}$;

Mass spectrometry (FAB): 440.12 [M+H$^+$].

EXAMPLE 5

5-methylfuro[3,4-c]pyrrolo[3,4-a]carbazole-1,3,4,6 (2H,5H,7H)-tetrone

The expected product is obtained in accordance with the procedure described in, Example 2, starting from the compound of Preparation D and N-methylmaleimide.

Melting point: 294° C. (decomposition).

IR (KBr) $v_{C=O}$=1775, 1840 cm$^{-1}$; $v_{NH}$=3370 cm$^{-1}$.

Mass spectrometry (FAB): 321.05 [M+H$^+$].

EXAMPLE 6

2-[2-(diethylamino)ethyl]-5-methyl-1H-dipyrrolo[3, 4-a:3,4-c]carbazole-1,3,4,6(2H,5H,7H)-tetrone hydrochloride N-N-diethylethylenediamine (0.132 mmol) is added dropwise to a solution of the compound of Example 5 (0.088 mmol) dissolved in 5.2 ml of anhydrous tetrahydrofuran. The mixture is heated at 65° C. for 4 days with the exclusion of light and then cooled and taken up in a mixture of an aqueous 1N hydrochloric acid solution (40 ml) and ethyl acetate. The organic product is extracted with ethyl acetate. The aqueous phase is taken up in ethyl acetate and the pH is adjusted to 12 by the addition of a,saturated aqueous sodium hydrogen carbonate solution. The organic product is extracted with ethyl acetate. The organic phases are combined, dried over magnesium sulphate and filtered, and the solvent is evaporated off in the cold. To a solution, cooled to 0° C., of the amine so obtained dissolved in 400 μl of methanol there is added dropwise an aqueous 1N hydrochloric acid solution (190 μl). The mixture is, stirred for 30 minutes. The solvent is evaporated off, allowing the expected product to be isolated.

Melting point: 184° C. (decomposition).

IR (KBr): $v_{C=O}$=1710, 1720, 1765, 1775 cm$^{-1}$; $v_{NH}$=3300–3600 cm$^{-1}$.

Mass spectrometry (FAB): 419.17 [M+H$^+$].

EXAMPLE 7

1H-pyrido[2,3-b]dipyrrolo[3,4-e:3,4-g]indole-1,3,4,6 (2H,5H,7H)-tetrone

The expected product is obtained in accordance with the procedure described in Example 2, starting from the compound of Preparation E and maleimide.

EXAMPLE 8

2-methyl-7-(2,3,4,6tetra-O-acetyl-β-D-glucopyranosyl)-1H-pyrido[2,3-b]dipyrrolo[3,4-e:3,4-g]indole-1, 3,4,6(2H,5H,7H)-tetrone The expected product is obtained in accordance with the procedure described in Example 2, starting from the compound of Preparation F and maleimide.

EXAMPLE 9

2-methyl-1H-pyrido[2,3-b]dipyrrolo[3,4-e:3,4-g] indole-1,3,4,6(2H,5H,7H)-tetrone A mixture of the compound of Preparation G (55.0 mg) and maleimide (25.9 mg) in xylene (5 ml) is heated at reflux for 20 hours. After cooling, the mixture is filtered and washed with xylene. The solid obtained (70.8 mg) is heated at reflux for 3 days in dioxane (5 ml) in the presence of 2,3-dichloro-5,6-dicyano-1,4-benzoquinone (115.5 mg). After removal of the solvent by evaporation, the residue is taken up in water and the solid obtained is filtered off and washed with water and ethyl acetate, allowing the expected product to be obtained.

Melting point: >300° C.

IR (KBr): $v_{C=C}$=1600 cm$^{-1}$; $v_{C=O}$=1710, 1730, 1770, 1780 cm$^{-1}$; $v_{NH}$=3200 cm$^{-1}$.

EXAMPLE 10

2-methylfuro[3,4-a]pyrrolo[3,4-c]carbazole-1,3,4,6 (2H,7H)-tetrone

A mixture of the compound of Preparation B (315 mg) and maleic anhydride (164 mg) in p-xylene (24 ml) is heated at reflux for 40 hours. After returning to ambient temperature, the mixture is filtered and the crystals are washed with p-xylene and then dried. The solid obtained (357 mg) is heated at reflux in dioxane (8 ml) for 3 days in the presence of 2,3-dichloro-5,6-dicyano-1,4-benzoquinone (540 mg). After returning to ambient temperature, water and with ethyl acetate are added. The solid at the interface is filtered off over a frit and washed with water and ethyl acetate, allowing the expected product to be isolated.

Melting point: >300° C.
IR (KBr): $v_{C=O}$=1705, 1760, 1835 cm$^{-1}$; $v_{NH}$=3770 cm$^{-1}$.

EXAMPLE 11

5-[2-(diethylamino)ethyl]-2-methyl-1H-dipyrrolo[3,4-a:3,4-c]carbazole-1,3,4,6(2H,5H,7H)-tetrone hydrochloride N-N-diethylethylenediamine (20 μl) is added dropwise to a solution of the compound of Example 10 in dry tetrahydrofuran (5.5 ml). The mixture is heated at 65° C. for 4 days with the exclusion of light. After returning to ambient temperature, the mixture is evaporated to dryness, taken up in 1 ml of acetic anhydride in the presence of AcONa (75 mg) and then heated at 90° C. for 4 hours. The crude reaction mixture is cooled and then taken up in a mixture of an aqueous 1N hydrochloric acid solution (40 ml) and ethyl acetate. The aqueous phase is then taken up in ethyl acetate and treated with an aqueous saturated sodium hydrogen carbonate solution. The organic product is then extracted with ethyl acetate (3×50 ml). The organic phases are combined and dried over magnesium sulphate and the solvent is evaporated off at room temperature. The free amine so obtained (32.8 mg) is taken up in methanol (1 ml) and then cooled to 0° C. An aqueous 1N hydrochloric acid solution (172 μl) is then added dropwise. The mixture is stirred for 30 minutes. The solvent is evaporated off, allowing the expected product to be obtained.

Melting point:=278–280° C.
IR (KBr): $v_{C=O}$=1710, 1770 cm$^{-1}$; $v_{NH}$=3200, 3600 cm$^{-1}$.

EXAMPLE 12

5-methyl-1H-dipyrrolo[3,4-a:3,4-c]carbazole-1,3,4,6 (2H,5H,7H)-tetrone

The expected product is obtained in accordance with the procedure described in Example 9, starting from the compound of Preparation A and with the replacement of maleimide by N-methylmaleimide.

Melting point: >300° C.
IR (KBr): $v_{C=O}$=1695, 1725, 1765, 1775 cm$^{-1}$ $v_{NH}$=3220, 3330 cm$^{-1}$.

EXAMPLE 13

Furo[3,4-a]pyrrrolo[3,4-c]carbazole-1,3,4,6(2H,7H)-tetrone

The expected product is obtained in accordance with the procedure described in Example 10, starting from the compound of Preparation A.

Melting point: >300° C.
IR (KBr): $v_{C=C}$=1610 cm$^{-1}$; $v_{C=O}$=1700–1850 cm$^{-1}$; $v_{NH}$=3240, 3380 cm$^{-1}$.

EXAMPLE 14

10-(benzyloxy)-1H-dipyrrolo[3,4-a:3,4-c]carbazole-1,3,4,6(2H,5H,7H)-tetrone

The expected product is obtained in accordance with the procedure described in Example 9, starting from the compound of Preparation H.

Melting point: >300° C.
IR (KBr): $v_{C=O}$=1725, 1755, 1780 cm$^{-1}$; $v_{NH}$=3150–3500 cm$^{-1}$.

EXAMPLE 15

10-bromo-1H-dipyrrolo[3,4-a:3,4-c]carbazole-1,3,4,6(2H,5H,7H)-tetrone

The expected product is obtained in accordance with the procedure described in Example 9, starting from the compound of Preparation I.

Melting point: >300° C.
IR (KBr): $v_{C=C}$=1600 cm$^{-1}$; $v_{C=O}$=1710, 1720, 1760 cm$^{-1}$; $v_{NH}$=3150–3350 cm$^{-1}$;

EXAMPLE 16

10-chloro-1H-dipyrrolo[3,4-a:3,4-c]carbazole-1,3,4,6(2H,5H,7H)-tetrone

The expected product is obtained in accordance with the procedure described in Example 9, starting from the compound of Preparation J.

Melting point: >300° C.
IR (KBr): $v_{C=C}$=1600 cm$^{-1}$; $v_{C=O}$=1710, 1720, 1760 cm$^{-1}$; $v_{NH}$=3120–3380 cm$^{-1}$.

EXAMPLE 17

10-fluoro-1H-dipyrrolo[3,4-a:3,4-c]carbazole-1,3,4,6(2H,5H,7H)-tetrone

The expected product is obtained in accordance with the procedure described in Example 9, starting from the compound of Preparation K.

Melting point: >300° C.
IR (KBr): $v_{V=O}$=1710, 1780cm$^{-1}$; $v_{NH}$=3100–3350cm$^{-1}$.

EXAMPLE 18

10-hydroxy-1H-dipyrrolo[3,4-a:3,4-c]carbazole-1,3,4,6(2H,5H,7H)-tetrone

The expected product is obtained in accordance with the procedure described in Example 9, starting from the compound of Preparation L.

Melting point: >300° C.

IR (KBr): $\nu_{C=O}$=1725, 1770 cm$^{-1}$; $\nu_{NH}$=3100–3650 cm$^{-1}$.

EXAMPLE 19

7-[1-(2,3,4,6-tetra-O-benzyl-β-D-glucopyranosyl)]-1H-dipyrrolo[3,4-a:3,4-c]carbazole-1,3,4,6(2H,5H,7H)-tetrone The expected product is obtained in accordance with the procedure described in Example 2, starting from the compound of Preparation M and maleimide.

EXAMPLE 20

7-(β-D-glucopyranosyl)-1H-dipyrrolo[3,4-a:3,4-c]carbazole-1,3,4,6(2H,5H,7H)-tetrone Debenzylation by BBr$_3$ of the compound of Example 19 in dichloromethane allows the expected compound to be obtained.

EXAMPLE 21

7-[1-(2,3,4,6-tetra-O-benzyl-β-D-glucopyranosyl)]-1H-pyrido[2,3-b]-dipyrrolo[3,4-e:3,4-g]carbazole-1,3,4,6(2H,5H,7H)-tetrone The expected product is obtained in accordance with the procedure described in Example 9, starting from the compound of Preparation N.

EXAMPLE 22

7-(β-D-glueopyranosyl)]-1H-pyrido[2,3-b]dipyrrolo[3,4-e:3,4-g]-indole-1,3,4,6(2H,5H,7H)-tetrone A 1M solution of BBr$_3$ in CH$_2$Cl$_2$ (8 eq.) is added to a solution of the compound of Example 21 in dichloromethane at −78° C. After 10 minutes'stirring at −78° C., the reaction mixture is hydrolysed and brought to ambient temperature, and then extracted repeatedly with ethyl acetate. The organic phase is dried over magnesium sulphate and then concentrated under reduced pressure. Chromatography on silica gel allows the expected product to be isolated.

The products of Examples 23 to 50 are obtained according to the procedure described in Example 9, starting from the compounds of Preparations O to AP, respectively.

EXAMPLE 23

10-amino-1H-dipyrrolo[3,4-a:3,4-c]carbazole-1,3,4,6(2H,5H,7H)-tetrone

EXAMPLE 24

11-amino-1H-dipyrrolo[3,4-a:3,4-c]carbazole-1,3,4,6(2H,5H,7H)-tetrone

EXAMPLE 25

9,10-dimethoxy-1H-dipyrrolo[3,4-a:3,4-c]carbazole-1,3,4,6(2H,5H,7H)-tetrone

EXAMPLE 26

11-nitro-1H-dipyrrolo[3,4-a:3,4-c]carbazole-1,3,4,6(2H,5H,7H)-tetrone

EXAMPLE 27

11-fluoro-1H-dipyrrolo[3,4-a:3,4-c]carbazole-1,3,4,6(2H,5H,7H)-tetrone

EXAMPLE 28

9-fluoro-1H-dipyrrolo[3,4-a:3,4-c]carbazole-1,3,4,6(2H,5H,7H)-tetrone

EXAMPLE 29

11-hydroxy-1H-dipyrrolo[3,4-a:3,4-c]carbazole-1,3,4,6(2H,5H,7H)-tetrone

EXAMPLE 30

10-hydroxy-1H-dipyrrolo[3,4-a:3,4-c]carbazole-1,3,4,6(2H,5H,7H)-tetrone

EXAMPLE 31

11-methoxy-1H-dipyrrolo[3,4-a:3,4-c]carbazole-1,3,4,6(2H,5H,7H)-tetrone

EXAMPLE 32

10-methoxy-1H-dipyrrolo[3,4-a:3,4-c]carbazole-1,3,4,6(2H,5H,7H)-tetrone

EXAMPLE 33

9-methoxy-1H-dipyrrolo[3,4-a:3,4-c]carbazole-1,3,4,6(2H,5H,7H)-tetrone

EXAMPLE 34

8-methoxy-1H-dipyrrolo[3,4-a:3,4-c]carbazole-1,3,4,6(2H,5H,7H)-tetrone

EXAMPLE 35

11-methyl-1H-dipyrrolo[3,4-a:3,4-c]carbazole-1,3,4,6(2H,5H,7H)-tetrone

EXAMPLE 36

10-methyl-1H-dipyrrolo[3,4-a:3,4-c]carbazole-1,3,4,6(2H,5H,7H)-tetrone

EXAMPLE 37

9-methyl-1H-dipyrrolo[3,4-a:3,4-c]carbazole-1,3,4,6(2H,5H,7H)-tetrone

EXAMPLE 38

8-methyl-1H-dipyrrolo[3,4-a:3,4-c]carbazole-1,3,4,6(2H,5H,7H)-tetrone

EXAMPLE 39

11-chloro-1H-dipyrrolo[3,4-a:3,4-c]carbazole-1,3,4,6(2H,5H,7H)-tetrone

EXAMPLE 40

10-chloro-1H-dipyrrolo[3,4-a:3,4-c]carbazole-1,3,4,6(2H,5H,7H)-tetrone

EXAMPLE 41

9-chloro-1H-dipyrrolo[3,4-a:3,4-c]carbazole-1,3,4,6(2H,5H,7,H)-tetrone

EXAMPLE 42

8-chloro-1H-dipyrrolo[3,4-a:3,4-c]carbazole-1,3,4,6(2H,5H,7H)-tetrone

EXAMPLE 43

11-bromo-1H-dipyrrolo[3,4-a:3,4-c]carbazole-1,3,4,6(2H,5H,7H)-tetrone

EXAMPLE 44

9-bromo-1H-dipyrrolo[3,4-a:3,4-c]carbazole-1,3,4,6(2H,5H,7H)-tetrone

EXAMPLE 45

8-bromo-1H-dipyrrolo[3,4-a:3,4-c]carbazole-1,3,4,6(2H,5H,7H)-tetrone

EXAMPLE 46

10-methoxy-11-methyl-1H-dipyrrolo[3,4-a:3,4-c]carbazole-1,3,4,6(2H,5H,7H)-tetrone

EXAMPLE 47

8-(benzyloxy)-1H-dipyrrolo[3,4-a:3,4-c]carbazole-1,3,4,6(2H,5H,7H)-tetrone

EXAMPLE 48

9-(benzyloxy)-1H-dipyrrolo[3,4-a:3,4-c]carbazole-1,3,4,6(2H,5H,7H)-tetrone

EXAMPLE 49

10-(benzyloxy)-9-methoxy-1H-dipyrrolo[3,4-a:3,4-c]carbazole-1,3,4,6(2H,5H,7H)-tetrone

EXAMPLE 50

7-methyl-1H-dipyrrolo[3,4-a:3,4-c]carbazole-1,3,4,6(2H,5H,7H)-tetrone

EXAMPLE 51

2-hydroxy-5-methyl-1H-dipyrrolo[3,4-a:3,4-c]carbazole-1,3,4,6(2H,5H,7H)-tetrone

The expected product is obtained in accordance with the procedure described in Example 6, with the replacement of N,N-diethylethylenediamine by hydroxylamine.

EXAMPLE 52

2-amino-5-methyl-1H-dipyrrolo[3,4-a:3,4-c]carbazole-1,3,4,6(2H,5H,7H)-tetrone

The expected product is obtained in accordance with the procedure described in Example 6, with the replacement of N,N-diethylethylenediamine by hydrazine.

EXAMPLE 53

2-(dimethylamino)-5-methyl-1H-dipyrrolo[3,4-a:3,4-c]carbazole-1,3,4,6(2H,5H,7H)-tetrone The expected product is obtained in accordance with the procedure described in Example 6, with the replacement of N,N-diethylethylenediamine by 1,1-dimethylhydrazine.

EXAMPLE 54

2-(3-hydroxypropyl)-5-methyl-1H-dipyrrolo[3,4-a:3,4-c]carbazole-1,3,4,6(2H,5H,7H)-tetrone The expected product is obtained in accordance with the procedure described in Example 6, with the replacement of N,N-diethylethylenediamine by 3-amino-1-propanol.

EXAMPLE 55

2-(3-methoxypropyl)-5-methyl-1H-dipyrrolo[3,4-a:3,4-c]carbazole-1,3,4,6(2H,5H,7H)-tetrone The expected product is obtained in accordance with the procedure described in Example 6, with the replacement of N,N-diethylethylenediamine by 3-methoxypropylamine.

PHARMACOLOGICAL STUDY OF THE COMPOUNDS OF THE INVENTION

EXAMPLE 56

In Vitro Activity

Three cell lines were used:
L1210 murine leukaemia
A549 non-small-cell human lung carcinoma
DU145 prostate carcinoma L1210 murine leukaemia was used in vitro. The cells are cultured in RPMI 1640 complete culture medium containing 10% foetal calf serum, 2 mM glutamine, 50 units/ml of penicillin, 50 μg/ml of streptomycin and 10 mM Hepes, pH: 7.4. The cells are distributed on microplates and are exposed to the cytotoxic compounds for 4 doubling periods, or 48 hours. The number of viable cells is then quantified by a colorimetric assay, the Microculture Tetrazolium Assay (J. Carmichael et al., *Cancer Res.*; 47, 936–942 (1987)). The results are expressed as the $IC_{50}$, the concentration of cytotoxic agent that inhibits the proliferation of the treated cells by 50%. By way of example, the compound of Example 2 exhibits $IC_{50}$ values of 6.8 μM on L1210, 4.7 μM on A549 and 5.4 μM on DU 145.

EXAMPLE 57

Pharmaceutical Composition: Injectable Solution

Compound of Example 1 . . . 10 mg
Distilled water for injectable preparations . . . 25 ml

What is claimed is:

1. A compound selected from those of formula (I):

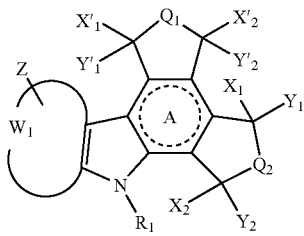

wherein:

A represents a saturated or partially or fully unsaturated ring, wherein the unsaturation optionally confers an aromatic nature on the ring, $W_1$, together with the carbon atoms to which it is bonded, represents phenyl or pyridyl, Z represents one or more identical or different groups of formula U—V wherein:

U represents a single bond, linear or branched ($C_1$–$C_6$) alkylene, linear or branched ($C_2$–$C_6$)alkenyl optionally substituted by one or more identical or different groups selected from halogen and hydroxy, and/or optionally containing one or more unsaturated bonds, V represents a group selected from hydrogen, halogen, cyano, nitro, azido, linear or branched ($C_1$–$C_6$)alkyl, aryl, aryl-($C_1$–$C_6$)alkyl in which the alkyl moiety may be linear or branched, hydroxy, linear or branched ($C_1$–$C_6$)alkoxy, aryloxy, aryl-($C_1$–$C_6$) alkoxy in which the alkoxy moiety may be linear or branched, formyl, carboxy, aminocarbonyl, $NR_3R_4$, —C(O)-$T_1$, —C(O)—NR$_3$-$T_1$, NR$_3$—C(O)-$T_1$, —O—C(O)-$T_1$, —C(O)—O-$T_1$, —NR$_3$-$T_2$-NR$_3R_4$, —NR$_3$-$T_2$-OR$_3$, —NR$_3$-$T_2$-CO$_2R_3$, —O-$T'_2$-NR$_3R_4$, —O-$T'_2$-OR$_3$, —O-$T'_2$-CO$_2R_3$, and —S(O)$_t$-$R_3$, wherein $R_3$ and $R_4$, which may be indentical or different, each represents a group selected from hydrogen, linear or branched ($C_1$–$C_6$)alkyl, aryl, and aryl-($C_1$–$C_6$)alkyl in which the alkyl moiety may be linear or branched, or $R_3$ and $R_4$, together with the nitrogen atom carrying them, form a saturated monocyclic or bicyclic heterocycle that has from 5 to 10 ring atoms, and which optionally contains in the ring system a second hetero atom selected from oxygen and nitrogen, and which is optionally substituted by a group selected from linear or branched ($C_1$–$C_6$)alkyl, aryl, aryl-($C_1$–$C_6$)alkyl in which the alkyl moiety may be linear or branched, hydroxy, linear or branched ($C_1$–$C_6$)alkoxy, amino, linear or branched mono-($C_1$–$C_6$)alkylamino, and di($C_1$–$C_6$)alkylamino in which the alkyl moieties may be linear or branched, $T_1$ represents a group selected from linear or branched ($C_1$–$C_6$)alkyl which may be optionally substituted by a group selected from —OR$_3$, —NR$_3R_4$, —CO$_2R_3$, —C(O)R$_3$ and —C(O)NR$_3R_4$ wherein $R_3$ and $R_4$ are as defined hereinbefore; aryl, and aryl-($C_1$–$C_6$)alkyl in which the alkyl moiety may be linear or branched; or $T_1$ represents linear or branched ($C_2$–$C_6$)alkenyl optionally substituted by a group selected from —OR$_3$, —NR$_3R_4$, —CO$_2R_3$, —C(O)R$_3$ and —C(O)NR$_3R_4$ wherein $R_3$ and $R_4$ are as defined hereinbefore, $T_2$ represents linear or branched ($C_1$–$C_6$)alkylene, $T'_2$ represents a linear or branched ($C_1$–$C_6$)alkylene optionally substituted with one ore more hydroxy groups, t represents integer of from 0 to 2 inclusive, or Z represents methylenedioxy or ethylenedioxy, $Q_1$ represents a group selected from oxygen, NR$_2$, wherein R$_2$ represents a group selected from hydrogen, linear or branched ($C_1$–$C_6$)alkyl, aryl, aryl-($C_1$–$C_6$) alkyl in which the alkyl moiety may be linear or branched, cycloalkyl, cycloalkyl-($C_1$–$C_6$)alkyl in which the alkyl moiety may be linear or branched, —OR$_3$, —NR$_3R_4$, —O-$T_2$-NR$_3R_4$, —NR$_3$-$T_2$NR$_3R_4$, linear or branched ($C_1$–$C_6$)hydroxyalkylamino, di(($C_1$–$C_6$)hydroxyalkyl)amino, in which the alkyl moieties may be linear or branched, —C(O)—R$_3$ and —NH—C(O)—R$_3$; or R$_2$ represents linear or branched ($C_1$–$C_6$)alkylene substituted by one or more identical or different groups selected from halogen, cyano, nitro, —OR$_3$, —NR$_3R_4$, —CO$_2R_3$, —C(O)R$_3$, linear or branched ($C_1$–$C_6$)hydroxyalkylamino, di(($C_1$–$C_6$)hydroxyalkyl)amino, in which the alkyl moieties may be linear or branched, and —C(O)—NHR$_3$, R$_3$, R$_4$ and T$_2$ being as defined hereinbefore, $Q_2$ represents a group selected from oxygen, NR'$_2$, wherein R'$_2$ represents a group selected from hydrogen, linear or branched ($C_1$–$C_6$)alkyl, aryl, aryl-($C_1$–$C_6$) alkyl, in which the alkyl moiety may be linear or branched, cycloalkyl, cycloalkyl-($C_1$–$C_6$)alkyl, in which the alkyl moiety may be linear or branched, —OR$_3$, —NR$_3R_4$, —O-$T_2$-NR$_3R_4$, —NR$_3$-$T_2$-NR$_3R_4$, linear or branched ($C_1$–$C_6$)hydroxyalkylamino, di(($C_1$–$C_6$)hydroxyalkyl)amino, in which the alkyl moieties may be linear or branched, —C(O)—R$_3$ and —NH—C(O)—R$_3$; or R'$_2$ represents a linear or branched ($C_1$–$C_6$)alkylene substituted by one or more identical or different groups selected from halogen, cyano, nitro, —OR$_3$, —NR$_3R_1$, —CO$_2R_3$, —C(O)R$_3$, linear or branched ($C_1$–$C_6$)hydroxyalkylamino, di(($C_1$–$C_6$)hydroxyalkyl)amino, in which the alkyl moieties may be linear or branched, and —C(O)—NHR$_3$, R$_3$, R$_4$ and T$_2$ being as defined hereinbefore, $X_1$ represents a group selected from hydrogen, hydroxy, linear or branched ($C_1$–$C_6$)alkoxy, mercapto, and linear or branched ($C_1$–$C_6$)alkylthio, $Y_1$ represents hydrogen, or $X_1$ and $Y_1$, with carbon carrying them, together form carbonyl or thiocarbonyl, $X_2$ represents a group selected from hydrogen, hydroxy, linear or branched ($C_1$–$C_6$)alkoxy, mercapto and linear or branched ($C_1$–$C_6$)alkylthio, $Y_2$ represents hydrogen, or $X_2$ and $Y_2$, with carbon carrying them, together form carbonyl or thiocarbonyl, $X'_1$ represents a group selected from hydrogen, hydroxy, linear or branched ($C_1$–$C_6$)alkoxy, mercapto and linear or branched ($C_1$–$C_6$)alkylthio, $Y'_1$ represents hydrogen, or $X'_1$ and $Y'_1$, with carbon carrying them, together form carbonyl or thiocarbonyl, $X'_2$ represents a group selected from hydrogen, hydroxy, linear or branched ($C_1$–$C_6$)alkoxy, mercapto and linear or branched ($C_1$–$C_6$)alkylthio, $Y'_2$ represents hydrogen, or $X'_2$ and $Y'_2$, with carbon carrying them, together form carbonyl or thiocarbonyl, $R_1$ represents a group selected from hydrogen, linear or branched ($C_1$–$C_6$)alkyl which may be optionally substituted by one or more groups selected from hydroxy, linear or branched ($C_1$–$C_6$)alkoxy, linear or branched ($C_1$–$C_6$)hydroxyalkoxy or $NR_3R_4$, the groups $R_3$ and $R_4$ being as defined hereinbefore; or $R_1$ represents a group of formula (a):

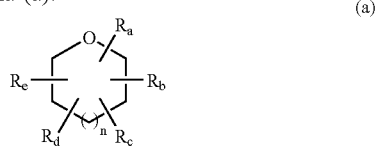

wherein:

$R_a$, $R_b$, $R_c$ and $R_d$, which may be identical or different, each represents, independently of the others, a bond or a group selected from hydrogen, halogen, hydroxy, linear or branched ($C_1$–$C_6$)alkoxy, aryloxy, aryl-($C_1$–$C_6$)alkoxy in which the alkoxy moiety may be linear or branched, linear or branched ($C_1$–$C_6$) alkyl, aryl-($C_1$–$C_6$)alkyl in which the alkyl moiety may be linear or branched, aryl, —$NR_3R_4$ wherein $R_3$ and $R_4$ are as defined hereinbefore, azido, —N=$NR_3$ (wherein $R_3$ is as defined hereinbefore), —O—C(O)—$R_5$ wherein $R_5$ represents linear or branched ($C_1$–$C_6$)alkyl (optionally substituted by one or more groups selected from halogen, hydroxy, amino, linear or branched ($C_1$–$C_6$)alkylamino, and di($C_1$–$C_6$)alkylamino in which the alkyl moieties may be linear or branched); or $R_5$ represents aryl, aryl-($C_1$–$C_6$)alkyl in which the alkyl moiety may be linear or branched, cycloalkyl or heterocycloalkyl, $R_e$ represents methylene ($H_2C$=) or a group of formula —$U_1$—$R_a$ wherein $U_1$ represents single bond, methylene and $R_a$ is as defined hereinbefore, n is 0 or 1, it being understood that the group of formula (a) is bonded to the nitrogen atom by $R_a$, $R_b$, $R_c$, $R_d$ or $R_e$, its enantiomers, diastereoisomers, and addition salts thereof with a pharmaceutically acceptable acid or base, with the proviso that the compound may not be:

3b,6a,6b,7-tetrahydro-1H-dipyrrolo[3,4-a:3,4-c]carbazole-1,3,4,6-(2H,3aH,5H)-tetrone;

5-ethyl-3b,6a,6b,7-tetrahydro-1H-dipyrrolo[3,4-a:3,4-c]carbazole-1,3,4,6-(2H,3aH,5H)-tetrone;

3b,6a,7,11c-tetrahydro-1H-dipyrrolo[3,4-a:3,4-c]carbazole-1,3,4,6-(2H,3aH,5H)-tetrone;

3b,6a,6b,7-tetrahydrofuro[3,4-a]pyrrolo[3,4-c]carbazole-1,3,4,6-(2H,3aH,5H)-tetrone;

wherein aryl is understood to mean a phenyl, naphthyl, dihydronaphthyl, tetrahydronaphthyl, indenyl or indanyl group, each of those groups optionally being substituted by one or more identical or different groups selected from halogen, linear or branched ($C_1$–$C_6$) alkyl, linear or branched ($C_1$–$C_6$)trihaloalkyl, hydroxy, linear or branched ($C_1$–$C_6$)alkoxy, and $NR_3R_4$, $R_3$ and $R_1$ being as defined hereinbefore.

2. A compound of claim 1, wherein $X_1$ and $Y_1$, with the carbon carrying them, together form carbonyl, $X_2$ and $Y_2$, with the carbon carrying them, together form carbonyl, $X'_1$ and $Y'_1$, with the carbon carrying them, together form carbonyl and $X'_2$ and $Y'_2$, with the carbon carrying them, together form carbonyl.

3. A compound of claim 1 wherein $Q_1$ represents —$NR_2$.

4. A compound of claim 1 wherein $Q_2$ represents —$NR'_2$.

5. A compound of claim 1 which is a compound of formula (IA):

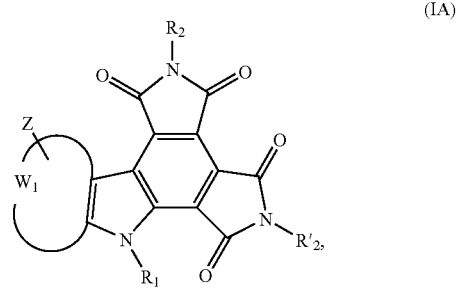

wherein $R_1$, $R_2$, $R'_2$, $W_1$, and Z are as defined in claim 1.

6. A compound of claim 1 which is a compound of formula (IB):

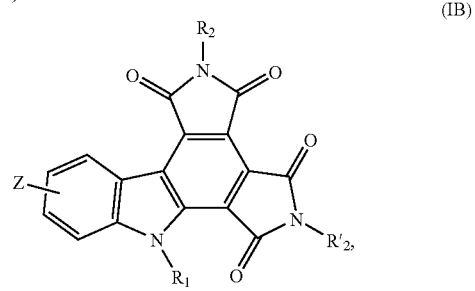

wherein $R_1$, $R_2$, $R'_2$, and Z are as defined in claim 1.

7. A compound of claim 1 which is a compound of formula (IC):

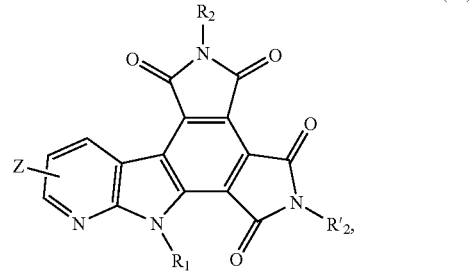

wherein $R_1$, $R_2$, $R'_2$, and Z are as defined in claim 1.

8. A compound of claim 1 which is a compound of formula (ID):

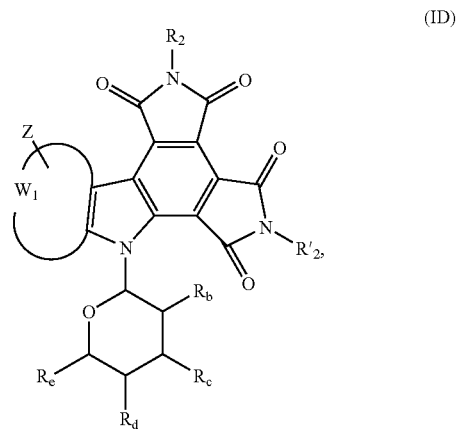

wherein $R_2$, $R'_2$, $W_1$, Z, $R_b$, $R_c$, $R_d$, and $R_e$ are as defined in claim 1.

9. A compound of claim 1 which is a compound of formula (IE):

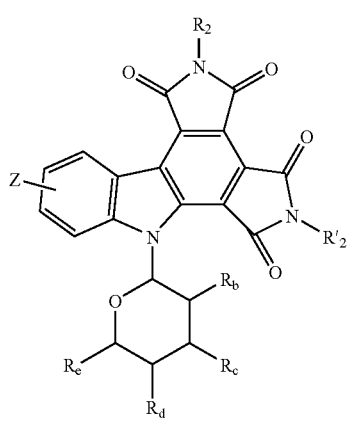

(IE)

wherein $R_2$, $R'_2$, Z, $R_b$, $R_c$, $R_d$, and $R_e$ are as defined in claim 1.

10. A compound of claim 1 which is a compound of formula (IF):

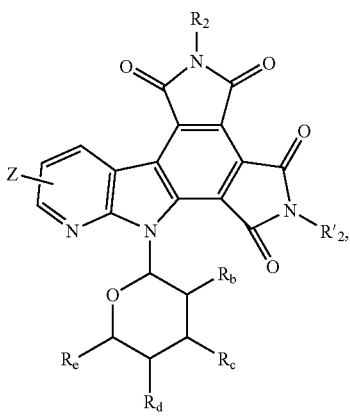

(IF)

wherein $R_2$, $R'_2$, Z, $R_b$, $R_c$, $R_d$, and $R_e$ are as defined in claim 1.

11. A compound of claim 1 wherein Z represents a group of formula U—V wherein U represents single bond and V represents a group selected from hydrogen, halogen, nitro, linear or branched ($C_1$–$C_6$)alkyl, hydroxy, linear or branched ($C_1$–$C_6$)alkoxy, aryl-($C_1$–$C_6$)alkoxy in which the alkoxy moiety may be linear or branched, $NR_3R_1$, wherein $R_3$ and $R_4$ each represents a hydrogen atom.

12. A compound of claim 1 wherein Z represents a group of formula U—V wherein U represents single bond and V represents a group selected from hydrogen, halogen, hydroxy, aryl-($C_1$–$C_6$)alkoxy in which the alkoxy moiety may be linear or branched.

13. A compound of claim 1 wherein $R_1$ represents hydrogen, linear or branched ($C_1$–$C_6$)alkyl or a group of formula (a):

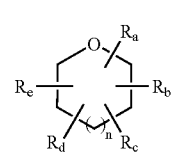

(a)

bonded to the nitrogen atom by Ra,
wherein:
$R_b$, $R_c$, and $R_d$ represent hydroxy, aryl-($C_1$–$C_6$)alkoxy in which the alkoxy moiety may be linear or branched, —O—C(O)—$R_5$ wherein $R_5$ represents linear or branched ($C_1$–$C_6$)alkyl,
$R_e$ represents a group of formula $U_1$—$R_a$ wherein $U_1$ represents methylene and $R_a$ has the same definitions as $R_b$, $R_c$ and $R_d$ and n is 0.

14. A compound of claim 1 wherein $R_1$ represents hydrogen.

15. A compound of claim 1 wherein $R_2$ represents hydrogen, linear or branched ($C_1$–$C_6$)alkyl, $OR_3$, $NR_3R_4$, or linear or branched ($C_1$–$C_6$)alkylene substituted by $OR_3$, $NR_3R_4$ wherein $R_3$ and $R_4$ are as defined for formula (I).

16. A compound of claim 1 wherein $R_2$ represents hydrogen, linear or branched ($C_1$–$C_6$)alkyl, linear or branched ($C_1$–$C_6$)alkylene substituted by $NR_3R_4$ wherein $R_3$ and $R_4$ are as defined for formula I.

17. A compound of claim 1 wherein $R'_2$ represents hydrogen, linear or branched ($C_1$–$C_6$)alkyl, linear or branched ($C_1$–$C_6$)alkylene substituted by $NR_3R_4$ wherein $R_3$ and $R_4$ are as defined for formula (I).

18. A compound of claim 1 which is selected from:
1H-dipyrrolo[3,4-a:3,4-c]carbazole-1,3,4,6(2H,5H,7H)-tetrone,
2-methyl-1H-dipyrrolo[3,4-a:3,4-c]carbazole-1,3,4,6(2H,5H,7H)-tetrone,
2,5-dimethyl-1H-dipyrrolo[3,4-a:3,4-c]carbazole-1,3,4,6(2H,5H,7H)-tetrone,
2-[2-(diethylamino)ethyl]-5-methyl-1H-dipyrrolo[3,4-a:3,4-c]carbazole-1,3,4,6(2H,5H,7H)-tetrone, and
10-hydroxy-1H-dipyrrolo[3,4-a:3,4-c]carbazole-1,3,4,6(2H,5H,7H)-tetrone.

19. A method for treating a living animal body afflicted with a condition selected from leukaemia, lung carcinoma, and prostate carcinoma, comprising the step of administering to the living animal body an amount of a compound of claim 1, which is effective for alleviation of the condition.

20. A pharmaceutical composition comprising as active principle an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO.       : 7,151,108 B2
APPLICATION NO.  : 10/672418
DATED            : December 19, 2006
INVENTOR(S)      : Michelle Prudhomme et al.

It is certified that error appears in the above-identified patent and that said Letters Patent is hereby corrected as shown below:

Cover Page, Item (73) Assignee: "Les Laboratories Servier" should be --Les Laboratoires Servier--.

Column 32, Line 36:   "-$NR_3R_1$" should be --$NR_3R_4$--.

Column 33, Line 58:   "$R_1$" should be --$R_4$--.

Column 35 Formula (IF):

"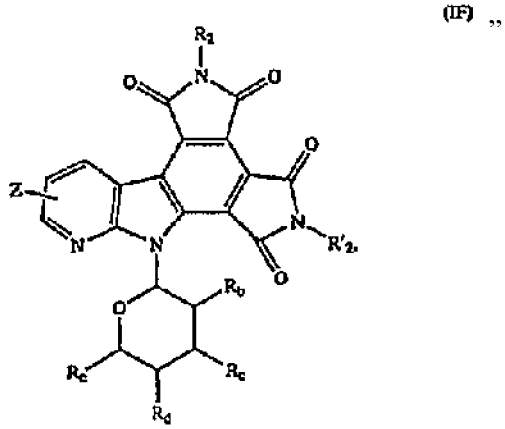 (IF) ,,

Should Be

-- 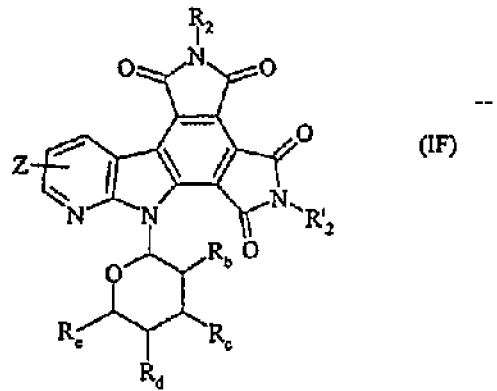 (IF) --

UNITED STATES PATENT AND TRADEMARK OFFICE
CERTIFICATE OF CORRECTION

PATENT NO.         : 7,151,108 B2
APPLICATION NO. : 10/672418
DATED              : December 19, 2006
INVENTOR(S)        : Michelle Prudhomme et al.

It is certified that error appears in the above-identified patent and that said Letters Patent is hereby corrected as shown below:

Column 35, Line 54: "-$NR_3R_1$" should be --$NR_3R_4$--.

Signed and Sealed this

Tenth Day of April, 2007

JON W. DUDAS
*Director of the United States Patent and Trademark Office*